United States Patent
Nielsen et al.

(10) Patent No.: US 9,719,057 B2
(45) Date of Patent: Aug. 1, 2017

(54) LAUNDRY DETERGENT

(71) Applicant: Liquid Vanity ApS, Aalborg Ø (DK)

(72) Inventors: Dan Mønster Nielsen, Ebeltoft (DK); Per Bendix Jeppesen, Egå (DK); Allan Korsgaard Poulsen, Hasselager (DK)

(73) Assignee: Liquid Vanity ApS (DK)

( * ) Notice: Subject to any disclaimer, the term of this patent is extended or adjusted under 35 U.S.C. 154(b) by 0 days.

(21) Appl. No.: 14/870,316

(22) Filed: Sep. 30, 2015

(65) Prior Publication Data

US 2016/0017262 A1    Jan. 21, 2016

Related U.S. Application Data

(63) Continuation of application No. 13/636,573, filed as application No. PCT/DK2011/050099 on Mar. 25, 2011, now abandoned.

(30) Foreign Application Priority Data

Mar. 26, 2010  (DK) .................................. 2010 70128

(51) Int. Cl.
*C11D 3/48* (2006.01)
*C11D 1/66* (2006.01)
(Continued)

(52) U.S. Cl.
CPC ............... *C11D 3/48* (2013.01); *A01N 25/02* (2013.01); *A01N 33/12* (2013.01); *A01N 47/40* (2013.01);
(Continued)

(58) Field of Classification Search
None
See application file for complete search history.

(56) References Cited

U.S. PATENT DOCUMENTS

| | | | |
|---|---|---|---|
| 2,438,091 A | 3/1948 | Lynch | 260/482 |
| 2,528,378 A | 10/1950 | Mannheimer et al. | 260/309.6 |

(Continued)

FOREIGN PATENT DOCUMENTS

| | | | |
|---|---|---|---|
| CN | 1 313 036 | 9/2001 | ............. A01N 47/40 |
| EP | 1 240 300 B1 | 12/2000 | ............... C11D 3/39 |

(Continued)

OTHER PUBLICATIONS

Lambert et al., "Theory of antimicrobial combinations: biocide mixtures—synergy or addition", Journal of Applied Microbiology 2003, 94, pp. 747-759).*

(Continued)

*Primary Examiner* — Ernst V Arnold
*Assistant Examiner* — Kyung Sook Chang
(74) *Attorney, Agent, or Firm* — Sunstein Kann Murphy & Timbers LLP

(57) ABSTRACT

A biocidal composition is provided, which comprise a mixture of the biocides Poly-(hexamethylene-guanidium chloride) and N,N-didecyl-N-methyl-poly(oxyethyl) ammonium propionate, which biocides have a synergistic biocidal effect against bacteria and fungi. Specifically, the provided composition can be as disinfectants and general biocidal products; preservatives; pest control; control; preservatives for food or feedstocks; antifouling products; embalming and taxidermist fluids; and control of other vertebrates; vermin control on domestic animals, livestock or pets; alga control; and products for use in spas or swimming pools.

34 Claims, 3 Drawing Sheets

Figure 1:
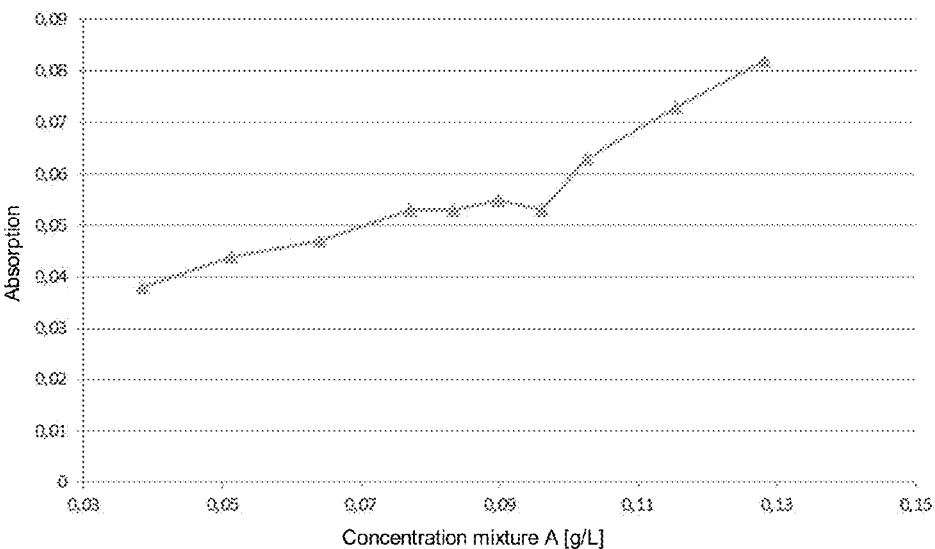

(51) Int. Cl.

| | |
|---|---|
| *A01N 25/02* | (2006.01) |
| *A01N 33/12* | (2006.01) |
| *A01N 47/40* | (2006.01) |
| *C11D 1/38* | (2006.01) |
| *C11D 3/37* | (2006.01) |
| *C11D 11/00* | (2006.01) |
| *C11D 1/72* | (2006.01) |
| *C11D 1/62* | (2006.01) |
| *C11D 1/835* | (2006.01) |

(52) U.S. Cl.
CPC .................. *C11D 1/38* (2013.01); *C11D 1/66* (2013.01); *C11D 1/72* (2013.01); *C11D 1/835* (2013.01); *C11D 3/3723* (2013.01); *C11D 11/0017* (2013.01); *C11D 1/62* (2013.01)

(56) References Cited

U.S. PATENT DOCUMENTS

| | | | | |
|---|---|---|---|---|
| 2,658,072 | A | 11/1953 | Kosmin | 260/513 |
| 3,929,678 | A | 12/1975 | Laughlin et al. | 252/526 |
| 4,755,327 | A | 7/1988 | Bernarducci et al. | 252/547 |
| 5,104,646 | A | 4/1992 | Bolich, Jr. et al. | 424/70 |
| 5,106,609 | A | 4/1992 | Bolich, Jr. et al. | 424/70 |
| 6,090,768 | A | 7/2000 | Delaney et al. | 510/325 |
| 6,693,069 | B2 | 2/2004 | Körber et al. | 510/310 |
| 2002/0115581 | A1 | 8/2002 | DuVal et al. | 510/276 |
| 2003/0045443 | A1 | 3/2003 | Korber et al. | 510/302 |
| 2005/0036982 | A1 | 2/2005 | Unhoch et al. | 424/78.27 |
| 2006/0030516 | A1 | 2/2006 | Demeyere et al. | 510/521 |
| 2006/0276468 | A1 | 12/2006 | Blow | 514/232.5 |
| 2008/0015134 | A1 | 1/2008 | Ahmed et al. | 510/234 |
| 2008/0138385 | A1 | 6/2008 | Fukatsu et al. | 424/443 |

FOREIGN PATENT DOCUMENTS

| | | | | |
|---|---|---|---|---|
| EP | 1 627 646 A1 | 2/2006 | | A61L 2/16 |
| FR | 2 295 122 A1 | 7/1976 | | C11D 3/48 |
| JP | 63310803 A2 | 12/1988 | | A01N 43/40 |
| JP | 2002327199 A | 11/2002 | | C11D 17/08 |
| RU | 2263708 C2 | 11/2005 | | A16L 2/18 |
| WO | WO 97/44422 A1 | 11/1997 | | C11D 1/835 |
| WO | WO 01/93684 A2 | 12/2001 | | A01N 47/44 |
| WO | WO 2006/067439 A1 | 6/2006 | | C11D 3/18 |
| WO | WO 2008/129026 A1 | 10/2008 | | C11D 1/65 |
| WO | WO 2011/116775 A2 | 9/2011 | | C11D 1/72 |
| WO | WO 2011/116775 A3 | 9/2011 | | C11D 1/72 |

OTHER PUBLICATIONS

Authorized Officer: Eric Péntek, International Search Report and the Written Opinion of the International Searching Authority; PCT/DK2011/050099, Jan. 23, 2012.

Bergqvist, Mette of Hoiberg, Response to Written Opinion, International Application No. PCT/DK2011/050099 dated, 9 pages, Apr. 23, 2012.

Braga et al., "Crystal Polymorphism and Multiple Crystal Forms," Structure Bond, 132: pp. 25-50, Feb. 2009.

European Patent Office, International Preliminary Report on Patentability for International Application No. PCT/DK2011/050099 together with the Written Opinion of the International Searching Authority, 15 pages, Jul. 16, 2012.

Fijan et al., "Antimicrobial Disinfection Effect of a Laundering Procedure for Hospital Textiles Against Various Indicator Bacteria and Fungi Using Different Substrates for Simulating Human Excrements," *Diagnostic Microbiology and Infectious Disease*, 57, pp. 251-257, Mar. 2007.

Lonza group, Product information: Bardap-26, 2 pages, retrieved online, http://www.oversiz.ru/d/16404/d/bardap26piseng1002.pdf, Oct. 2002.

Ozzie Chemical (Dalian) Co., Ltd., Ozzie Product Information, http://www.ozzietrade.com/news.asp?id=55, Oct. 7, 2008.

Slee et al., "Relationship Between Structure and Antiplaque and Antimicrobial Activities for a Series of Bispyridines," *Antimicrobial Agents and Chemotherapy—American Society for Microbiology*, pp. 531-535, Apr. 1983.

* cited by examiner

LAUNDRY DETERGENT

CROSS REFERENCE TO RELATED APPLICATIONS

This application is a continuation of U.S. application Ser. No. 13/636,573 filed Dec. 14, 2012, which in turn is the U.S. National Stage of PCT/DK2010/050099, filed Mar. 25, 2011 which in turn claims priority to Denmark Patent Application No. PA 201070128, filed Mar. 26, 2010. The entire contents of all of the above related applications are incorporated herein by reference.

FIELD OF INVENTION

The present invention relates to a laundry detergent composition, preferably a delicate laundry detergent, comprising one or more biocidal compounds for washing of textiles and materials, where washing at low temperature is desired at the same time as obtaining a biocidal effect, as for example lingerie and underwear.

BACKGROUND OF INVENTION

When washing clothing fully or in part made of delicate natural fabrics like silk or wool there may be a conflict between the desire to protect and care for the fabrics and the desire to obtain clean clothing. This may especially be relevant when the clothes in question are such as lingerie or underwear.

Traditionally, underwear, bed sheets or kitchen towels have been washed at temperatures of 60 or 95° C., in order to obtain both visually and hygienic clean laundry. Over the years laundry detergent product have been developed that comprise enzymes, such as proteases, amylases, lipases, and cellulases; these laundry detergents are marketed for washing at lower temperatures such as 30 or 40° C. as the enzymes aids in the washing process. Recently, low-temperature detergents have been developed that may be used at temperatures as low as 15-20° C., these contain newly developed enzymes aiding the washing process.

In the particular case with wool and silk textiles, the natural polymer on which the textile fiber is based is a protein and thus susceptible to degradation by the enzyme. In fact, depending on the enzyme and the washing conditions, there is a real risk of the fabrics being gradually eaten by the enzymes. Enzyme based detergents are not recommended for wool and silk containing textiles.

Presence of microorganisms in textiles or other materials may provide a health hazard. The Danish National Consumer Agency has stated that it in certain instances is necessary to do laundry at 95° C. This is for example in cases of infectious diseases, in cases with particularly dirty textiles, such as diapers, and when laundering textiles comprising sources of infection. Such sources of infection may be faeces, urine, blood, body fluids, etc. The temperature of 95° C. is to ensure elimination of such sources of infection, which modern enzyme containing laundry detergents suitable for washing at e.g. 40° C. do not ensure.

There has recently furthermore been an increased focus on the possibility of cross-contamination from one batch of laundry to the next. If for instance one person has used a washing machine on e.g. 40° for textiles carrying a source of infection, and the next person uses the same washing machine for washing at low temperature as well, e.g. delicate textiles such as lingerie at 30° C., there may be transferred microorganisms from one laundry batch to the next. This is for example a risk in apartment blocks with communal laundries, at launderettes, or especially at communal laundries in nursing homes or hospitals with a majority of ill or frail persons susceptible both to provide the infection or easily gain an infection from cross-contaminated clothes, bed linen or towels washed in a communal laundry.

Accordingly, in order to obtain a satisfying laundry of e.g. lingerie or underwear, it is necessary to wash at at least 60° C. However, the manufactures of lingerie, or other delicate textiles, provide care labels prescribing a washing temperature of 40° C. or less. The lack of washing at sufficiently high temperature gives rise to the above-mentioned problems of cross-contamination or an actually continued re-infection of the same person. This may for instance be the case with genital fungal infections that in some may become chronic, or vaginitis in general, such as e.g. both candidiasis or bacterial vaginosis. Sources of infection are for example bacteria (such as e.g. *Streptococcus, Staphylococcus aureus, Gardnerella, Escherichia coli*, bacteriods, or *mycoplasma*), fungi (such as e.g. *Candida albicans*), or vira (such as e.g. HIV-1, Hepatitis B or Hepatitis C).

In addition to being sensitive towards enzymes, wool and silk textiles also need to be washed at low temperatures of for example 30 or 40° C. and at gentle cycle in washing machine or gently by hand wash, in order to avoid excessive shrinkage or deformation. It is further recommended to avoid heavily alkaline pH. Therefore, a laundry detergent for delicate fabrics, such as silk and wool, needs to be enzyme free, less alkaline than traditional laundry detergents and suitable for washing at low temperatures.

The above stated problems with cross-contamination or re-infection are therefore especially relevant for such delicate textiles. Accordingly, unless the clothing items are only lightly soiled and there is no risk of infectious sources, there is a conflict between caring for the fabric and obtaining clean clothing. When the clothing items are such as lingerie or underwear there is special need for a delicate laundry detergent that in addition to washing and caring for the fabric also can remove any undesired remains of bacteria, fungi or vira.

Due to the chemical nature of both laundry detergent ingredients and biocidal compounds, it is well-known that not all combinations of such ingredients may provide a stable and effective composition that both provides detergent and biocidal properties.

Another well-known problem in the field of cleaning products is that rather high concentrations of products comprising a single biocide are required and that the target microorganisms are likely to get resistant towards the biocide used upon long-term treatment.

SUMMARY OF INVENTION

The inventors of the present invention have now surprisingly succeeded in identifying a biocide composition comprising one or more biocides having synergistic effect thus minimizing the concentration required to obtain biocidal effect. Use of a 2 component biocidal composition may also reduce the risk that the microorganisms to be targeted get resistant towards the biocide composition.

The inventors of the present invention have furthermore surprisingly succeeded in providing stable detergent compositions comprising one or more biocides and one or more surfactants.

The biocidal composition according to the invention have many different uses, one of which is as a laundry composition. Other non-limiting uses for a biocidal composition according to the invention is e.g. in:

Disinfectants and general biocidal products such as in human hygiene biocidal products; private area and public health area disinfectants and other biocidal products; veterinary hygiene biocidal products; and food and feed area disinfectants and drinking water disinfectants;

Preservatives such as in in-can preservatives; film preservatives; wood preservatives; fibre, leather, rubber and polymerised materials preservatives; masonry preservatives; preservatives for liquid-cooling and processing systems, slimicides; textiles and metalworking-fluid preservatives;

Pest control such as in rodenticides; avicides; molluscicides; pesticides; insecticides, acaricides and products to control other arthropods; and repellents and attractants;

Other biocidal products such as in preservatives for food or feedstocks; antifouling products; embalming and taxidermist fluids; and control of other vertebrates;

Vermin such as in or on domestic animals, livestock or pets;

Alga; and

Products for use in e.g. spas, swimming pools and the like.

In another embodiment the present invention relates to a laundry detergent composition, such as preferably a delicate laundry detergent composition, comprising one or more biocidal compounds. The composition is preferably for washing textiles or materials made fully or in part of silk or wool, or other enzyme sensitive materials such as natural hair.

The composition is furthermore preferably a liquid laundry detergent, and may comprise one or more biocidal compounds selected from the group consisting of a PQ polymer, Poly(hexamethylenebiguanide) hydrochloride, Akacid Forte®, Akacid®, N,N-didecyl-N-methyl-poly(oxyethyl) ammonium propionate (Bardap-26), povidone-iodine (PVP-iodine, Betadine™); benzyl $C_{12-18}$-alkyldimethyl ammonium chlorides, benzyl $C_{12-14}$-alkyldimethyl ammonium chlorides, $C_{12-13}$-alkyl[(ethylphenyl)methyl]dimethyl ammonium chlorides (ADBAC), di-$C_{8-10}$alkyldimethyl ammonium chloride (DDAC), and Octenidine dihydrochloride; or toxicological acceptable salts or solvates thereof.

In another preferred embodiment of the invention the one or more biocidal compounds is a synergistic combination which may be used as such or as part of a composition also comprising one or more surfactants.

In one preferred embodiment of the invention the one or more biocidal compounds is a synergistical combination of one or more biocidal compound, providing an increased biocidal effect compared to use of either biocidal compound alone in same total concentration. In an especially preferred embodiment of the invention the biocidal compound is a mixture of Akacid Forte® and Bardap-26.

DETAILED DESCRIPTION OF THE INVENTION

One aspect of the invention relates to a biocidal composition, which have many different uses, one of which is as a laundry composition. Other non-limiting uses for a biocidal composition according to the invention is e.g. in:

Disinfectants and general biocidal products such as in human hygiene biocidal products; private area and public health area disinfectants and other biocidal products; veterinary hygiene biocidal products; and food and feed area disinfectants and drinking water disinfectants;

Preservatives such as in in-can preservatives; film preservatives; wood preservatives; fibre, leather, rubber and polymerised materials preservatives; masonry preservatives; preservatives for liquid-cooling and processing systems, slimicides; and metalworking-fluid preservatives;

Pest control such as in rodenticides; avicides; molluscicides; pesticides; insecticides, acaricides and products to control other arthropods; and repellents and attractants; and Other biocidal products such as in preservatives for food or feedstocks; antifouling products; embalming and taxidermist fluids; and control of other vertebrates;

Vermin such as in or on domestic animals, livestock or pets;

Alga; and

Products for use in e.g. spas, swimming pools and the like.

In one embodiment of the invention, the biocidal composition of the invention comprises at least two biocides having synergistic effect. In one embodiment, the biocidal composition of the invention does not comprise a surfactant. In another embodiment of the invention, the biocidal composition of the invention comprises one or more surfactants.

The inventors of the present invention surprisingly succeeded in defining the optimal biocidal detergent composition. Accordingly, the inventors found that stability problems of biocidal compositions comprising one or more surfactants were due to micelle formation and that such micelle formation which be avoided by carefully selecting a nonionic or monovalent cationic surfactants. The inventors found that the most preferred detergent composition comprises surfactants such as nonionic or monovalent cationic surfactants such as of the general formula $R(OCH_2CH_2)_xOH$ wherein:

R is $C_{7-20}$-alkyl whereby the alkyl is of 7-20 carbon atoms wherein R may optionally be substituted as defined herein; and x is 2-12 whereby the polyethyleneglycol comprises 2-12 repetitions of $OCH_2CH_2$.

Micelle formation leads to encapsulation of biocide thus preventing the detergent composition comprising one or more biocides to have efficient biocidal effect. Accordingly, by preventing micelle formation, an efficient biocidal effect of the detergent composition comprising one or more biocides can be maintained.

The inventors of the present invention also realized that the micelle formation may be avoided and thus that stable detergent compositions may be obtained if the critical micelle concentration of the one or more biocides (CMC (biocid)) is higher than the minimum inhibitory concentration of the one or more biocides (MIC(biocid)).

The inventors of the present invention also realized that the micelle formation may be avoided and thus that stable detergent compositions may be obtained if the critical micelle concentration of the detergent composition (CMC (detergent)) is higher than the minimum inhibitory concentration of the one or more biocides (MIC(biocid)).

The inventors furthermore succeeded in identifying a surprisingly efficient synergistic biocide composition comprising two or more biocides. When comprised in a biocidal detergent composition, convincing results have been obtained in that the biocidal effect of the biocide composition comprising two or more biocides is not influenced by the presence of surfactants in said biocidal detergent composition.

The inventors of the present invention succeeded in providing biocidal detergent compositions reducing the total amount of fungus with a factor $10^5$ or more. In one embodiment of the invention, the total amount of fungus was even reduced with a factor $10^6$. The inventors of the present invention furthermore succeeded in providing biocidal detergent compositions reducing the total amount of bacteria with a factor $10^7$ or more. The convincing reduction in fungus and bacteria thus obtained was highly surprising.

The same reduction in bacteria growth or yeast growth was obtained independently of the soap tested, however only as long as the soap comprised a surfactant of the formula $R(OCH_2CH_2)_x(OH$ wherein:

R is $C_{7-20}$-alkyl whereby the alkyl is of 7-20 carbon atoms wherein R may optionally be substituted as defined herein; and and x is 2-12 whereby the polyethyleneglycol comprises 2-12 repetitions of $OCH_2CH_2$.

Is has also been shown that a biocidal detergent composition wherein the surfactant comprises $C_{18}$-alkyl and wherein the one or more surfactants in addition to $(OCH_2CH_2)_xOH$ also comprises $(OCH_2CH_2CH_2)_x$ only reduced the growth of microorganisms insignificantly in that only a reduction of $10^2$ was obtained.

One aspect of the invention relates to the use of a biocidal composition according to the invention, with or without detergent, e.g. in:

Disinfectants and general biocidal products such as in human hygiene biocidal products; private area and public health area disinfectants and other biocidal products; veterinary hygiene biocidal products; and food and feed area disinfectants and drinking water disinfectants;

Preservatives such as in in-can preservatives; film preservatives; wood preservatives; fibre, leather, rubber and polymerised materials preservatives; masonry preservatives; preservatives for liquid-cooling and processing systems, slimicides; and metalworking-fluid preservatives;

Pest control such as in rodenticides; avicides; molluscicides; pesticides; insecticides; acaricides and products to control other arthropods; and repellents and attractants;

Other biocidal products such as in preservatives for food or feedstocks; antifouling products; embalming and taxidermist fluids; and control of other vertebrates;

Vermin such as in or on domestic animals, livestock or pets;

Alga; and

Products for use in e.g. spas, swimming pools and the like.

One aspect of the invention relates to a product which is a biocidal composition as such, i.e. a composition which does not comprise detergent. In a preferred embodiment, said biocidal composition without detergent comprises two or more biocides according to the invention, said biocides having synergistic effect. In one specific embodiment, said product is selected from the group consisting of disinfectants and general biocidal products. In another specific embodiment, said product is a preservative. In yet another specific embodiment, said product is a product for pest control. In yet another embodiment, said product is selected from the group consisting of other biocidal products. In yet another specific embodiment, said product is a product for treatment of vermin. In yet another specific embodiment, said product is a product for control of alga. In yet another specific embodiment, said product is for use for disinfection, such as for disinfection of spas, swimming pools and the like.

One aspect of the present invention relates to a laundry detergent composition, such as preferably a delicate laundry detergent composition, comprising one or more biocides.

It is an objective of the present invention to provide a laundry detergent composition that may give, in addition to a detergent effect, a biocidal effect in order to eliminate or reduce the presence of microorganisms in textiles or materials that are not suitable for washing at high temperatures of 60° C. or 95° C.

It is furthermore an object of the present invention to provide a laundry detergent that may give, in addition to a detergent effect, a biocidal effect in order to eliminate or reduce the presence of microorganisms in textiles or materials, such as bed linen or towels from hospitals or nursing homes, that normally could be washed at high temperatures of 95° C., for elimination of sources of infection, but due to environmental considerations or practical considerations, such as lack of power, machinery etc in e.g. developing countries, preferably should be washed at lower temperatures.

The term "laundry detergent", as used herein, is intended to mean compositions for washing textiles or materials (e.g. clothing, towels, other household textiles or wigs) includes both solid and liquid detergent compositions, such as washing powder and liquid laundry detergent, unless otherwise stated. The term does not comprise dish washing detergents or other household cleaning agents.

In order to provide an easy to use consumer friendly product the laundry detergent of the present invention is preferably an all-in-one product. Accordingly, the active ingredients for washing and the one or more biocidal compounds are preferably in one and the same formulation, as opposed to a biocidal composition that is added before, during or after the actual washing process. An all-in-one product provides several advantages, for example being easy to use and fail-safe, i.e. the product is used as an ordinary laundry detergent not requiring knowledge of e.g. soaking time, or incompatibility between product and detergents.

The terms "delicate wash", "fine-fabric detergent", and "delicate laundry detergent", as used herein, are intended to mean a laundry detergent for washing delicate textiles or materials, such as e.g. lingerie, underwear, wool underwear, thermal underwear, stockings, tights, natural and/or synthetic wigs, bedclothes, duvets or related clothing or textile items, made fully or in part of silk, wool or other natural fibres (such as hair and feathers) sensitive towards traditional washing powders or liquid laundry products containing enzymes. Unless otherwise stated the delicate wash includes both solid and liquid compositions. In one specific embodiment of the present invention the laundry detergent, such as a delicate laundry detergent, do not comprise enzymes. A preferred embodiment of the present invention relates to a delicate laundry detergent; more preferably a delicate laundry detergent for washing of textiles or materials made fully or in part of silk, wool, hair, feathers or other natural fibers; even more preferably a delicate laundry detergent for washing of textiles or materials made fully or in part of silk, wool, hair or feathers; and yet even more preferably a delicate laundry detergent for washing of textiles or materials made fully or in part of silk or wool.

In addition to being sensitive towards enzymes, wool, silk and other natural materials need to be washed at low temperatures. The laundry detergent composition, and especially the delicate laundry detergent composition, according to the present invention may preferably be suitable for washing at low temperatures in a range of about 5° C. to about 40° C., more preferably of about 10° C. to about 40° C., such as for example of about 15° C. to about 40° C., of about 20° C. to about 40° C., of about 20° C. to about 40° C., of about 15° C. to about 30° C., of about 20° C. or of about 30° C. In an embodiment of the invention, the laundry detergent composition, and especially the delicate laundry detergent composition, according to the present invention may preferably be suitable for washing at low temperatures in a range of about 20° C. to about 40° C., such as about 25° C. to about 35° C. In a particular embodiment, of the invention, the laundry detergent composition, and especially the delicate laundry detergent composition, according to the present invention may preferably be suitable for washing at low temperatures in a range of about 30° C. When the term "suitable for washing" at a specified temperature is used herein in relation to the laundry detergent composition, it is intended to mean that the composition is effective at that temperature, both with respect to the detergent properties and the biocidal properties.

In one embodiment of the present invention, the laundry detergent composition is for use in washing of clothing or textiles considered to be a source of infection, such as preferably hospital or nursing home laundry. In said embodiment it is preferred to use one or more biocides that eliminate especially $E.\ coli$ fully, i.e. reduces the number of microorganisms by at least $10^6$, more preferably by $10^7$ or more. The present inventors have surprisingly found that by using a mixture of the biocides Bardap-26 and Akacid Forte® a synergistically effect is obtained at low concentrations and even at low temperature i.e. 30° C. Hereby eliminating the need for washing at at least 75° C. to obtain the same result with traditional laundry detergent compositions. See for example S. Fijan et al. for a study of the temperature, time and detergent needed to reduce/eliminate representative bacteria and fungi (Fijan et al.: *Antimicrobial disinfection effect of a laundering procedure for hospital textiles against various indicator bacteria and fungi using different substrates for simulating human excrements*; Diagnostic Microbiology and Infectious Disease; 57 (2007) 251-257).

The terms "washing powder" and "solid detergent", as used herein, are intended to mean a laundry detergent in solid, granular or powder form, and these terms may be used interchangeably.

The laundry detergent according to the present invention may be suitable for both machine wash and hand wash. Alternatively, the detergent composition may be specifically suitable for machine wash or specifically suitable for hand wash.

The terms "liquid laundry", "liquid laundry detergent" and "laundry washing liquid", as used herein, are intended to mean a laundry detergent in liquid form, as opposed to a solid detergent, and these terms may be used interchangeably. In a preferred embodiment of the present invention the laundry detergent composition, such as a delicate laundry detergent, is a liquid detergent composition.

The terms "biocide" or "biocidal compound", as used herein, are intended to mean a compound that eliminates or significantly reduces the growth of microorganisms. The terms may be used interchangeably herein and includes, unless otherwise stated, antimicrobial compounds, such as e.g. germicides, antibiotics, antibacterials, antivirals, antifungals, antiprotozoals and antiparasites. The microorganisms to be effected by these compounds may preferably be bacteria, vira or fungi; more preferably bacteria and fungi. It is an object of the present invention to provide a laundry composition that may eliminate or significantly reduce the growth of microorganisms selected from the group consisting of bacteria (such as e.g. *Streptococcus, Gardnerella, Staphylococcus aureus, Escherichia coli*, bacteriods, or *mycoplasma*), fungi (such as e.g. *Candida albicans*), and vira (such as e.g. HIV-1, Hepatitis B or Hepatitis C). The biocidal effect of a laundry detergent according to the present invention may for instance be assayed against a group of representative microorganisms such as e.g. *Staphylococcus aureus, Escherichia coli*, and *Candida albicans*.

Biocides

The one or more biocides to be used in the present invention may be one or more biocides approved for both human hygiene products and approved for use in private area and public health area products, as the present invention is to be used in private household laundry and at the same time may come in contact with the person wearing the clothing having been washed with a composition according to the present invention.

Such approved biocides may dependent on the geographical region and thereby on the authority in charge of the approval procedure. For Europe this is at present the European Commission and the listings of biocides can be found in the Biocidal Products Directive 98/8/EC. For some geographical regions no listings of approved biocides exist, in such cases there may instead be a negative list of biocides that may not be used. For such geographical regions the biocides to be used in the present invention may be a biocide not present on a negative list. In addition to being approved, or not being present on a negative list, it is important that the biocides are compatible with the laundry detergent. In one embodiment of the invention the biocide is not benzalkonium chloride.

It is furthermore an object of the present invention to provide a laundry detergent composition, wherein the one or more biocides are two or more biocides that together provide a synergistic effect on the elimination or reduction of microorganisms. By utilizing two different biocidal compounds, where one for example is especially effective towards bacteria and the other is especially effective towards fungi, a synergistic effect may be obtained with regard to the total biocidal activity. Hereby obtaining a number of advantages of the composition according to the invention, such as for example a reduction in the amount of total biocide present in the composition, and at the same time obtain a superior effect on the total amount of microorganisms.

In one embodiment of the present invention the total amount of microorganisms, preferably bacteria and fungi, are reduced by at least 50%, preferably at least 60%, more preferably at least 70%, even more preferably at least 80%, yet even more preferably at least 90%, and most preferably at least 99.9%. The reduction of microorganisms by the compositions of the present invention may preferably be determined according to the test described in the examples (see example 4A and 4B). The reduction in total amount of microorganisms may furthermore be expressed as a reduction in log units. It is an object of the present invention to utilize one or more biocidal compounds providing a reduction in fungus and bacteria of at least 3 and 4 log units, respectively, i.e. a reduction of $10^3$ and $10^4$; preferably of at least 4 and 5 log units ($10^4$ and $10^5$), respectively; more preferably of at least 5 and 6 log units ($10^5$ and $10^6$), respectively; and even more preferable of at least 6 and 7 log units ($10^6$ and $10^7$), respectively.

Under current practice, in order to accept a product as having a desinfective ability a reduction of at least $10^5$ (5 log units) of bacteria or at least $10^4$ (4 log units) reduction of yeast must be demonstrated (EN 1276:1997, DS/EN 1275:2005).

The biocidal effect may furthermore preferably be tested and defined as the effect on the following group of microorganisms: *Escherichia coli*, *Staphylococcus aureus*, *Pseudomonas aeruginosa*, and *Candida albicans*; or alternatively on the following group of microorganisms *Escherichia coli*, *Staphylococcus aureus*, and *Candida albicans*.

*Escherichia coli* have been chosen in order to represent a gram negative faecal bacteria; *Staphylococcus aureus* have been chosen in order to represent a gram positive, heat tolerant bacteria; *Pseudomonas aeruginosa* have been chosen in order to represent a disease causing bacteria that in some cases are difficult to treat; and *Candida albicans* represent the presence of fungi.

In one embodiment of the present invention the one or more biocide is effective for reducing *Escherichia coli*, *Staphylococcus aureus*, *Pseudomonas aeruginosa*, and *Candida albicans*.

In a particular embodiment of the invention, the one or more biocides according to the invention have a Minimum Inhibitory Concentration (MIC) of 1200 ppm or less. In an embodiment, the one or more biocides have a MIC of 700 ppm or less. In another embodiment, the one or more biocides have a MIC of 200 ppm or less. In yet another embodiment, the one or more biocides have a MIC of 160 ppm or less. In yet another embodiment, the one or more biocides have a MIC of 120 ppm or less. In yet another embodiment, the one or more biocides have a MIC of 80 ppm or less. In a preferred embodiment, the one or more biocides have a MIC of 40 ppm or less.

In one embodiment of the composition with or without detergent, the one or more biocides are comprised in a total amount of about 100-5000 ppm. In an embodiment thereof the one or more biocides are comprised in a total amount of about 100-2500 ppm; in an embodiment thereof the one or more biocides are comprised in a total amount of about 100-1000 ppm; in an embodiment thereof the one or more biocides are comprised in a total amount of about 150-800 ppm; in an embodiment thereof the one or more biocides are comprised in a total amount of about 200-700 ppm; in an embodiment thereof the one or more biocides are comprised in a total amount of about 20-100 ppm; and in a preferred embodiment thereof the one or more biocides are comprised in a total amount of about 250-600 ppm. Alternatively, the one or more biocides may be comprised in a total amount of less than 250 ppm, such as 250-200 ppm. In an embodiment thereof, the one or more biocides may be comprised in a total amount of less than 150 such as less than 100 ppm.

In one embodiment of the present invention the one or more biocides are selected from the group consisting of:
- a PQ polymer, such as e.g. polymeric quats, N,N-Dimethyl-2-hydroxypropylammonium chloride polymer (Barquat® PQ), from e.g. Lonza or The Polyquat Task Force;
- a polymeric biguanide polymer, such as e.g. PHMB, Poly(hexamethylenebiguanide) hydrochloride, Poly (hexamethylenguanidinium chloride) (Akacid Forte®), Poly(oxyalkyleneguanidine)hydrochloride (Akacid®);
- an alkyl and dialkyl oxyethylene methyl ammonium salt, such as e.g. N,N-didecyl-N-methyl-poly(oxyethyl) ammonium propionate (Bardap-26) or N,N-didecyl-N-methyl-poly(oxyethyl) ammonium lactate;
- povidone-iodine (PVP-iodine, Betadine™);
- an alkyl dimethyl benzyl ammonium salt or dialkyl methyl benzyl ammonium salt, such as e.g. Coco benzyl dimethyl ammonium chlorides or dicoco benzyl methyl ammonium chlorides with alkyl groups predominantly $C_{12-14}$, benzyl $C_{12-18}$-alkyldimethyl ammonium chlorides, benzyl $C_{12-14}$-alkyldimethyl ammonium chlorides, or $C_{12-13}$-alkyl[(ethylphenyl)methyl] dimethyl ammonium chlorides (ADBAC);
- a dialkyl dimethyl ammonium salt, such as e.g. di-$C_{8-10}$alkyldimethyl ammonium chloride, i.e. didecyl dimethyl ammonium chloride, dioctyl dimethyl ammonium chloride, or octyl decyl dimethyl ammonium chloride (DDAC); and
- a bispyridine, such as e.g. Octenidine dihydrochloride (see Slee et al., ANTIMICROBIAL AGENTS AND CHEMOTHERAPY, (1983), 23(4), p. 531-535, for further bispyridines); or toxicological acceptable salts or solvates thereof.

In one embodiment of the present invention the one or more biocides is selected from the group consisting of a PQ polymer; a polymeric biguanide polymer; an alkyl oxyethylene methyl ammonium salt; dialkyl oxyethylene methyl ammonium salt; povidone-iodine; an alkyl dimethyl benzyl ammonium salt; dialkyl methyl benzyl ammonium salt; a dialkyl dimethyl ammonium salt; and a bispyridine; or toxicological acceptable salts or solvates thereof.

In a more specific embodiment of the present invention one of the one or more biocides is a polymeric biguanide polymer, or toxicological acceptable salts or solvates thereof; and selected from the group consisting of PHMB, Poly(hexamethylenebiguanide) hydrochloride, Akacid Forte®, and Akacid®, or other toxicological acceptable salts or solvates thereof. In an even more specific embodiment of the present invention one of the one or more biocides is selected from the group consisting of Akacid Forte® and Akacid®, or mixtures thereof.

In another specific embodiment of the present invention one of the one or more biocides is an alkyl or dialkyl oxyethylene methyl ammonium salt, and selected from the group consisting of N,N-didecyl-N-methyl-poly(oxyethyl) ammonium propionate (e.g. Bardap-26) and N,N-didecyl-N-methyl-poly(oxyethyl) ammonium lactate. In an even more specific embodiment of the present invention one of the one or more biocides is Bardap-26.

In another specific embodiment of the present invention one or more biocides are selected from the group consisting of polymeric alk(an/en/yn)yl oxyethylene methyl ammonium salts, dialk(an/en/yn)yl oxyethylene methyl ammonium salts and biguanide polymers; or other toxicological acceptable salts or solvates thereof.

In another specific embodiment of the present invention one or more biocides is an alkyl oxyethylene methyl ammonium salt or dialkyl oxyethylene methyl ammonium salt such as N,N-didecyl-N-methyl-poly(oxyethyl) ammonium propionate (e.g. Bardap 26). The molar weight of the active ingredient (CAS nr. 94667-33-1) in Bardap-26 is about 454 g/mol.

In another specific embodiment of the present invention one or more biocides is a Poly-(hexamethylene-guanidium chloride) (e.g. Akacid Forte) or other toxicological acceptable salts or solvates thereof. The molar weight of the active ingredient (CAS nr. 57028-96-3) in Akacid Forte is about 1000 g/mol.

In another specific embodiment of the present invention one or more biocides is a mixture of poly-(hexamethylene-guanidium chloride) (e.g. Akacid Forte) and N,N-didecyl-N-methyl-poly(oxyethyl) ammonium propionate (e.g. Bardap 26).

In an embodiment of the invention, the one or more biocides is a mixture of poly-(hexamethylene-guanidium chloride) (e.g. Akacid Forte) and N,N-didecyl-N-methyl-poly(oxyethyl) ammonium propionate (e.g. Bardap 26) in a ratio of 0.5-1.5:1-5 by weight. In another embodiment of the invention, the one or more biocides is a mixture of poly-(hexamethylene-guanidium chloride) (e.g. Akacid Forte) and N,N-didecyl-N-methyl-poly(oxyethyl) ammonium propionate (e.g. Bardap 26) in a ratio of 0.8-1.2:2-4 by weight. In yet another embodiment of the invention, the one or more biocides is a mixture of poly-(hexamethylene-guanidium chloride) (e.g. Akacid Forte) and N,N-didecyl-N-methyl-poly(oxyethyl) ammonium propionate (e.g. Bardap 26) in a ratio of about 1:2 by weight. In a preferred embodiment of the invention, the one or more biocides is a mixture of poly-(hexamethylene-guanidium chloride) (e.g. Akacid Forte) and N,N-didecyl-N-methyl-poly(oxyethyl) ammonium propionate (e.g. Bardap 26) in a ratio of about 1:1 by weight. In yet another preferred embodiment of the invention, the one or more biocides is a mixture of poly-(hexamethylene-guanidium chloride) (e.g. Akacid Forte) and N,N-didecyl-N-methyl-poly(oxyethyl) ammonium propionate (e.g. Bardap 26) in a ratio of about 1:3 by weight.

In an embodiment of the invention, Poly-(hexamethylene-guanidium chloride) (e.g. Akacid Forte) and N,N-didecyl-N-methyl-poly(oxyethyl) ammonium propionate (e.g. Bardap 26) is p In a preferred embodiment of the present invention the one or more biocides is a mixture of Poly-(hexamethylene-guanidium chloride) (e.g. Akacid Forte®) and N,N-didecyl-N-methyl-poly(oxyethyl) ammonium propionate (e.g. Bardap-26), such as e.g. in a ratio of about 1:1, 1:1.25, 1:1.5, 1:1.75, 1:2, 1:3, 1:4, 1:5, 1.25:1, 1.5:1, 1.75:1, 2:1, 3:1, or 4:1; more preferably a mixture in a ratio of about 1:1, 1:1.25, 1:1.5, 1:1.75, 1:2, 1:3, 1.25:1, 1.5:1, 1.75:1, 2:1, or 3:1; even more preferably a mixture in a ratio of about 1:1, 1:1.25, 1:1.5, 1:1.75, 1:2, 1.25:1, 1.5:1, 1.75:1, or 2:1; yet even more preferably essentially a one to one mixture of Poly-(hexamethylene-guanidium chloride) (e.g. Akacid Forte®) and N,N-didecyl-N-methyl-poly(oxyethyl) ammonium propionate (e.g. Bardap-26). This specific combination of biocides has surprisingly been found to provide a synergistically effect in reducing all of the representative microorganisms *Escherichia coli*, *Staphylococcus aureus*, and *Candida albicans*. It is especially interesting that *Candida albicans*, which by the use of Akacid Forte alone in a concentration of 120 ppm was not reduced, and which by the use of Bardap-26 alone a concentration of 120 ppm was reduced by ~$10^3$, can be reduced by >$10^6$ by the use of a one to one mixture of the two in a total concentration of 120 ppm. Likewise it is interesting that *Staphylococcus aureus* which by the use of Akacid Forte alone in a concentration of 120 ppm was not reduced, and which by the use of Bardap-26 alone was reduced by $10^2$-$10^3$, can be reduced by >$10^6$ by the use of a one to one mixture of the two in a total concentration of 120 ppm. Furthermore, *Escherichia coli* may be reduced by >$10^6$ by the use of a one to one mixture of Bardap-26 and Akacid Forte in a concentration of e.g. 120 ppm, but may only be reduced by $10^4$-$10^6$ and ~$10^3$, respectively, by the use of the biocides alone. See Examples 4A and 4B herein for further details.

In another specific embodiment of the present invention one of the one or more biocides is povidone-iodine (PVP-iodine, Betadine™).

In another specific embodiment of the present invention one of the one or more biocides is an alkyl dimethyl benzyl ammonium salt or a dialkyl methyl benzyl ammonium salt; such as selected from the group consisting of Coco benzyl dimethyl ammonium chlorides or dicoco benzyl methyl ammonium chlorides with alkyl groups predominantly $C_{12-14}$, benzyl $C_{12-18}$-alkyldimethyl ammonium chlorides, benzyl $C_{12-14}$-alkyldimethyl ammonium chlorides, and $C_{12-13}$-alkyl[(ethylphenyl)methyl]dimethyl ammonium chlorides (ADBAC); more preferably $C_{12-13}$-alkyl[(ethylphenyl)methyl]dimethyl ammonium chlorides (ADBAC).

In another specific embodiment of the present invention one of the one or more biocides is a dialkyl dimethyl ammonium salt; such as di-$C_{8-10}$alkyldimethyl ammonium chloride; such as one or more selected from the group consisting of didecyl dimethyl ammonium chloride, dioctyl dimethyl ammonium chloride, and octyl decyl dimethyl ammonium chloride (DDAC).

In another specific embodiment of the present invention one of the one or more biocides is a bispyridine, or toxicological acceptable salts or solvates thereof; such as one or more bispyridine selected from the bispyridines specified in Slee et al., ANTIMICROBIAL AGENTS AND CHEMOTHERAPY, (1983), 23(4), p. 531-535; such as Octenidine dihydrochloride.

In another specific embodiment of the present invention one of the one or more biocides is a PQ polymer, or toxicological acceptable salts or solvates thereof; such as one or more polymeric quats, such as N,N-Dimethyl-2-hydroxypropylammonium chloride polymer (Barquat® PQ).

Biocides for use in the present invention may furthermore be quaternary ammonium compounds, such as one or more of the following:

1. Monoalkyltrimethyl ammonium salts, wherein the alkyl group e.g. is an alkyl with 6-18 carbon atoms, preferably 12-14 carbon atoms, and the salt is formed with an appropriate anion allowing ready water solubility, for example: chloride, bromide, sulphate, acetate, propionate, lactate, citrate, methosulphate and carbonate, preferred examples include $C_{12-14}$alkyl cocotrimethyl ammonium chloride;

2. Dialkyl dimethyl ammonium salts, wherein alkyl groups may be the same or different and contain 6-18 carbon atoms, preferably 8-10 carbon atoms, and the salt is formed with an anion of the type previously described, preferred examples include Didecyl dimethyl ammonium chloride, dioctyl dimethyl ammonium chloride and octyl decyl dimethyl ammonium chloride;

3. Alkyl dimethyl benzyl ammonium salts and dialkyl methyl benzyl ammonium salts, wherein alkyl groups may be the same or different and contain 6-18 carbon atoms, preferably 8-10 carbon atoms in a dialkyl and 10-14 carbon atoms in a monoalkyl, and the salt is formed with an anion of the type previously described, preferred examples include Coco benzyl dimethyl ammonium chloride and dicoco benzyl methyl ammonium chloride in which the alkyl groups predominantly are $C_{12-14}$;

4. Alkyl and dialkyl oxyethylene methyl ammonium salts, wherein alkyl groups may be the same or different and contain 6-18 carbon atoms, preferably 8-10 carbon atoms in a dialkyl and 10-14 carbon atoms in a monoalkyl, most preferably 10 carbon atoms, and the salt is formed with an anion of the type previously described, preferably propionate or lactate, preferred examples include N,N-didecyl-N-methyl-poly(oxyethyl) ammonium propionate (Bardap 26) or N,N-didecyl-N-methyl-poly(oxyethyl) ammonium lactate; and 5. Polymeric quaternary ammonium compounds in which active quaternary ammonium compounds are chemically grafted to a polymer backbone.

In an embodiment of the present invention the one or more biocides are selected from the group consisting of N,N-Dimethyl-2-hydroxypropylammonium chloride polymer (Barquat® PQ), Poly(hexamethylenebiguanide) hydrochloride, Poly(hexamethylenguanidinium chloride) (Akacid Forte®), Poly(oxyalkyleneguanidine)hydrochloride (Akacid®), N,N-didecyl-N-methyl-poly(oxyethyl) ammonium propionate (Bardap 26), povidone-iodine (PVP-iodine, Betadine™); benzyl $C_{12-18}$-alkyldimethyl ammonium chlorides, benzyl $C_{12-14}$-alkyldimethyl ammonium chlorides, $C_{12-13}$-alkyl[(ethylphenyl)methyl]dimethyl ammonium chlorides (ADBAC), di-$C_{8-10}$alkyldimethyl ammonium chloride (DDAC), and Octenidine dihydrochloride; or toxicological acceptable salts or solvates thereof.

The one or more biocides may be present in the composition according to the present invention in an amount of less than 20% by weight, in a range from between 0.01% to 15%, such as e.g. in a range from 0.01% to 12%, in a range from 0.10% to 10%, in a range from 0.10% to 8%, in a range from 0.5% to 8%, in a range from 1% to 8%, in a range from 1% to 6%, or in a range from 1% to 5% by weight. It is an objective of the present invention to reduce the amount of biocide present in order to meet environmental demands.

The amount of the one or more biocides may furthermore be expressed as amount present during use, i.e. when textiles are under the influence of the laundry detergent in an appropriate amount of water. This amount of biocide compound may be in a range from about 200 ppm to about 2 ppm, such as e.g. in a range from about 200 ppm to about 10 ppm or from about 200 ppm to about 20 ppm, more from about 180 ppm to about 20 ppm, such as e.g. about 180 ppm to about 40 ppm, even more from about 160 ppm to about 20 ppm, such as e.g. about 160 to about 40 ppm, yet even more from about 160 ppm to about 80 ppm, and yet even more form about 160 ppm to about 120 ppm, such as e.g. specifically about 120 ppm.

The amount of biocide is preferably reduced by using a combination of one or more biocides eliciting a synergistical effect on one or more representative microorganisms, such as for example *E. coli*, *Staphylococcus aureaus* and *Candida albicans*.

Detergent Compositions

The detergent composition according to the present invention may preferably, in addition to the one or more biocide, further comprise
i) one or more surfactants;
ii) one or more liquid carriers; and
iii) one or more chelating agents.

Furthermore, the detergent composition according to the present invention may preferably, in addition to the one or more biocide, further comprise
i) one or more surfactants;
ii) one or more liquid carriers;
iii) one or more chelating agents; and
iv) one or more detergent builders.

In an embodiment, the detergent compositions according to the invention comprises:
one or more liquid carriers in a total amount of about 60-95% (w/w); in an embodiment thereof the one or more liquid carriers are comprised in a total amount of about 70-90% (w/w); and in a preferred embodiment thereof the one or more liquid carriers are comprised in a total amount of about 75-85% (w/w); and
one or more chelating agents in a total amount of about 1-5% (w/w); in an embodiment thereof the one or more chelating agents are comprised in a total amount of about 2-4% (w/w); in a preferred embodiment thereof the one or more chelating agents are comprised in a total amount of about 3% (w/w);
one or more surfactants in a total amount of about 200-6000 ppm; in an embodiment thereof the one or more surfactants are comprised in a total amount of about 300-3000 ppm; in an embodiment thereof the one or more surfactants are comprised in a total amount of about 400-2000 ppm; in an embodiment thereof the one or more surfactants are comprised in a total amount of about 500-1500 ppm; in a preferred embodiment thereof the one or more surfactants are comprised in a total amount of about 600-1400 ppm; and
optionally, one or more biocides in a total amount of about 100-5000 ppm. In an embodiment thereof the one or more biocides are comprised in a total amount of about 100-2500 ppm; in an embodiment thereof the one or more biocides are comprised in a total amount of about 100-1000 ppm; in an embodiment thereof the one or more biocides are comprised in a total amount of about 150-800 ppm; in an embodiment thereof the one or more biocides are comprised in a total amount of about 200-700 ppm; in an embodiment thereof the one or more biocides are comprised in a total amount of about 20-100 ppm; and in a preferred embodiment thereof the one or more biocides are comprised in a total amount of about 250-600 ppm.

In a preferred embodiment of the biocidal detergent composition of invention, the one or more biocides fulfil the criterion that CMC(biocid)>MIC(biocid).

In another preferred embodiment of the biocidal detergent composition of invention, said detergent composition fulfil the criterion that CMC(detergent)>MIC(biocid).

Within the context of the present invention, MIC for yeast is the minimum inhibitory concentration at which a reduction of at least $10^3$ is obtained. In a preferred embodiment, MIC for yeast is the minimum inhibitory concentration at which a reduction of at least $10^4$ is obtained.

Within the context of the present invention, MIC for bacteria is the minimum inhibitory concentration at which a reduction of at least $10^4$ is obtained. In a preferred embodiment, MIC for bacteria is the minimum inhibitory concentration at which a reduction of at least $10^5$ is obtained.

The present detergent compositions may comprise as one essential component at least one surfactant selected from the group consisting of anionic surfactants, zwitterionic surfactants, amphoteric surfactants, nonionic surfactants, cationic surfactants such as monovalent cationic surfactants, and mixtures thereof. By nature, any surfactant known in the art of detergent compositions may be used, such as disclosed in (1) "Surfactant Science Series", Vol. 7, edited by W. M. Linfield, Marcel Dekker and in (2) "Surface—Active Agents & Detergents", Volumes I and II, by Schwatz, Perry and Berch. Suitable levels of this component are in the range from 1.0% to 80%, preferably from 5.0% to 65%, more preferably from 10% to 50% by weight of the composition.

In one embodiment, the biocidal detergent composition of the invention comprises surfactant:one or more biocides in a ratio of 2-12:1-5 by weight. In another embodiment, said biocidal detergent composition comprises surfactant:one or more biocides in a ratio of 5-9:2-4 by weight. In a preferred embodiment, said biocidal detergent composition comprises surfactant:one or more biocides in a ratio of about 7:3 (w/w).

A specific embodiment of the invention relates to a biocidal composition comprising water, propylene glycol, methylglycinediacetic acid (e.g. Trilon M), iso-C13 alcohol ethoxylate (e.g. Lutensol TO 89), N,N-didecyl-N-methylpoly(oxyethyl) ammonium propionate (e.g. Bardap 26) and poly-(hexamethylene-guanidium chloride) (e.g. Akacid Forte).

Another specific embodiment of the invention relates to a biocidal composition comprising water, propylene glycol, methylglycinediacetic acid (e.g. Trilon M), a mixture of fatty alcohols with 9 mol ethylene oxide and fatty alcohols with 3 mol ethylene oxide (e.g. Marlipal® 24/939), N,N-didecyl-N-methyl-poly(oxyethyl) ammonium propionate (e.g. Bardap 26) and poly-(hexamethylene-guanidium chloride) (e.g. Akacid Forte).

In an embodiment of the invention, the biocidal detergent composition according to the invention has a CMC of at least 0.5 mmol/l. In another embodiment, said CMC is at least 1 mmol/l. In another embodiment, said CMC is at least 1.5 mmol/l. In yet another embodiment, said CMC is at least 2 mmol/l. In yet another embodiment, said CMC is at least 2.5 mmol/l. In yet another embodiment thereof, said CMC is at least 3 mmol/l.

In en embodiment of the invention, the biocidal detergent composition according to the invention has a CMC of at least 0.02 g/l. In another embodiment, said CMC is at least 0.03 g/l. In yet another embodiment, said CMC is at least 0.05 g/l. In yet another embodiment, said CMC is at least 0.1 g/l. In yet another embodiment, said CMC is at least 0.15 g/l.

Surfactants

A surfactant according to the invention is preferably a nonionic or monovalent cationic surfactants and is preferably of the general formula I:

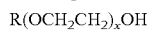

R(OCH$_2$CH$_2$)$_x$OH wherein
i) R is C$_{7-20}$-alkyl whereby the alkyl is of 7-20 carbon atoms; said R may optionally be substituted with one or more substituents selected from the group consisting of alkyl, C$_{3-8}$-cycloalkyl, C$_{3-8}$-cycloalkyl-C$_{1-6}$-alkyl, C$_{1-6}$-alkyl-C$_{3-8}$-cycloalkyl, aryl-C$_{1-6}$-alkyl, aryl, C$_{1-6}$-alkyl-aryl, aryl-C$_{1-6}$-alkyl, C$_{1-6}$-alkyl-oxy, C$_{3-8}$-cycloalkyl-oxy, C$_{3-8}$-cycloalkyl-C$_{1-6}$-alkyl-oxy, C$_{3-8}$-cycloalkyl-oxy-C$_{1-6}$-alkyl, C$_{1-6}$-alkyl-oxy-C$_{3-8}$-cycloalkyl, C$_{1-6}$-alkyl-C$_{3-8}$-cycloalkyl-oxy. aryl-C$_{1-6}$-alkyl-oxy and aryl, or R may optionally be substituted with one or two groups selected from R$_a$(OCH$_2$CH$_2$)$_y$OH and R$_b$(OCH$_2$CH$_2$)$_z$OH;
wherein
  a. Each of R$_a$ and R$_b$ are independently C$_{7-20}$-alkyl whereby the alkyl is of 7-20 carbon atoms;
  b. Each of y and z is 2-12 whereby the polyethyleneglycol comprises 2-12 repetitions of OCH$_2$CH$_2$; and
ii) and x is 2-12 whereby the polyethyleneglycol comprises 2-12 repetitions of OCH$_2$CH$_2$.
with the proviso that when R is C$_{18}$-alkyl then the surfactant may not comprise an alkoxylated moiety that comprises higher alkoxides than the ethylene oxides.

Within the context of the present invention, the term 'C$_{7-20}$-alkyl' refers to a branched or unbranched C$_{7-20}$-alkanyl, C$_{7-20}$-alkenyl or C$_{7-20}$-alkynyl group wherein:
  'C$_{7-20}$-alkanyl' refers to an alkanyl group that is 7-20 carbon atoms long;
  'C$_{7-20}$-alkenyl' designates an alkenyl groups that is 7-20 carbon atoms long; said group including one or more double bonds and
  'C$_{7-20}$-alkynyl' designates an alkynyl group that is 7-20 carbon atoms long, said group including one or more triple bonds.

Similarly, the term 'C$_{1-6}$-alkyl' refers to a branched or unbranched C$_{1-6}$-alkanyl, C$_{2-6}$-alkenyl or C$_{2-6}$-alkynyl wherein:
  C$_{1-6}$-alkanyl' refers to an alkanyl group that is 1-6 carbon atoms long;
  'C$_{2-6}$-alkenyl' designates an alkenyl groups that is 2-6 carbon atoms long; said group including one or more double bonds and
  'C$_{2-6}$-alkynyl' designates an alkynyl group that is 2-6 carbon atoms long, said group including one or more triple bonds.

The term 'C$_{3-8}$-cycloalkyl' refers to a C$_{3-8}$-cycloalkyl or a C$_{3-8}$-cycloalkenyl group wherein:
  'C$_{3-8}$-cycloalkanyl' designates a monocyclic or bicyclic carbocycle having three to eight C-atoms, including but not limited to cyclopropyl, cyclopentyl, cyclohexyl etc.; and
  'C$_{3-8}$-cycloalkenyl' designates a monocyclic or bicyclic carbocycle having three to eight C-atoms and one double bond, including but not limited to cyclopropenyl, cyclopentenyl, cyclohexenyl, etc.

The term 'aryl' refers to a carbocyclic aromatic group, such as phenyl or naphthyl.

The term 'C$_{1-6}$-alkyl-oxy' refers to groups of the formula C$_{1-6}$-alkyl-O— wherein C$_{1-6}$-alkyl is as defined above.

The term 'C$_{3-8}$-cycloalkyl-oxy' refers to groups of the formula C$_{3-8}$-cycloalkyl-O— wherein C$_{3-8}$-cycloalkyl is as defined above.

In the terms C$_{3-8}$-cycloalkyl-C$_{1-6}$-alkyl, C$_{1-6}$-alkyl-C$_{3-6}$-cycloalkyl, aryl-C$_{1-6}$-alkyl, C$_{1-6}$-alkyl-aryl, aryl-C$_{1-6}$-alkyl, C$_{1-6}$-alkyl-oxy, C$_{3-8}$-cycloalkyl-oxy, C$_{3-8}$-cycloalkyl-C$_{1-6}$-alkyl-oxy, C$_{3-8}$-cycloalkyl-oxy-C$_{1-6}$-alkyl, C$_{1-6}$-alkyl-oxy-C$_{3-8}$-cycloalkyl, C$_{1-6}$-alkyl-C$_{3-6}$-cycloalkyl-oxy. aryl-C$_{1-6}$-alkyl-oxy and aryl the terms C$_{1-6}$-alkyl, C$_{3-8}$-cycloalkyl, aryl, C$_{1-6}$-alkyl-oxy and C$_{3-8}$-cycloalkyl-oxy are as defined above.

Surfactants of general formula (I) may be prepared using conventional methods known to the person skilled in the art.

In one embodiment of the general formula I, x is 4-8 whereby the polyethylene glycol-moiety comprised in the surfactant in average has 4-8 repetitions of OCH$_2$CH$_2$.

In a preferred embodiment of the general formula I, x is 3-12 whereby the polyethylene glycol-moiety comprised in the surfactant in average has 3-12 repetitions of OCH$_2$CH$_2$.

In another preferred embodiment of formula I, x is 8.

In another preferred embodiment of formula I, x is selected from 3 and 9 and mixtures thereof.

In one embodiment of formula I, R is C$_{10-18}$-alkyl.

In one embodiment of formula I, R is C$_{12-14}$-alkyl. In one embodiment of formula I, R is C$_{12}$-alkyl. In one embodiment of formula I, R is C$_{13}$-alkyl. In one embodiment of formula I, R is C$_{14}$-alkyl.

In another embodiment of formula I, at least 80% by weight of R is C$_{12}$-alkyl, C$_{13}$-alkyl or C$_{14}$-alkyl or mixtures thereof. In one embodiment of formula I, R is C$_{10-18}$-alkyl.

In another embodiment of formula I, at least 90% by weight of R is C$_{12}$-alkyl, C$_{13}$-alkyl or C$_{14}$-alkyl or mixtures thereof. In one embodiment of formula I, 60-80% by weight, such as 65-75% by weight of R is C$_{12}$-alkyl. In another embodiment of formula I, 15-35% by weight, such as 20-30% by weight of R is C$_{14}$-alkyl. In a particular embodiment of formula I, 60-80% by weight, such as 65-75% by weight of R is C$_{12}$-alkyl. 15-35% by weight, such as 20-30% by weight of R is C$_{14}$-alkyl.

In one embodiment of formula I, no more than 5% by weight, such as less than 2% by weight and preferably less than 1% by weight of R is C$_{10}$-alkyl.

In one embodiment of formula I, no more than 5% by weight, such as less than 2% by weight, less than 1% and preferably less than 0.5% by weight of R is C$_{17-18}$-alkyl.

In one embodiment of formula I, no more than 5% by weight, such as less than 2% by weight, less than 1% and preferably less than 0.5% by weight of R is $C_{18}$-alkyl.

In one embodiment R is essentially not $C_{18}$-alkyl.

In one embodiment formula (I), R is substituted with one or more substituents selected from the group consisting of $C_{1-6}$-alk (en/yn)yl, $C_{3-8}$-cycloalk(en)yl, $C_{3-8}$-cycloalk(en)yl-$C_{1-6}$-alk(en/yn)yl, $C_{1-6}$-alk(en/yn)yl-$C_{3-8}$-cycloalk(en)yl, aryl-$C_{1-6}$-alk (en/yn)yl, aryl, $C_{1-6}$-alk (en/yn)yl-aryl, aryl-$C_{1-6}$-alk (en/yn)yl, $C_{1-6}$-alk (en/yn)yl-oxy, $C_{3-8}$-cycloalk(en)yl-oxy, $C_{3-8}$-cycloalk(en)yl-$C_{1-6}$-alk(en/yn)yl-oxy, $C_{3-8}$-cycloalk(en)yl-oxy-$C_{1-6}$-alk(en/yn)yl, $C_{1-6}$-alk(en/yn)yl-oxy-$C_{3-8}$-cycloalk(en)yl, $C_{1-6}$-alk(en/yn)yl-$C_{3-8}$-cycloalk(en)yl-oxy. aryl-$C_{1-6}$-alk (en/yn)yl-oxy and aryl-oxy-$C_{1-6}$-alk (en/yn)yl and aryl.

In another embodiment of formula (I), R is substituted with one or two groups selected from $R_a(OCH_2CH_2)_yOH$ and $R_b(OCH_2CH_2)_zOH$.

In yet another embodiment of formula (I), R is not substituted.

In an embodiment of the invention, the molar weight of a surfactant according to the invention is in the range of 100-1500 g/mol. In an embodiment thereof, the molar weight of a surfactant is in the range of 200-1000 g/mol. In an embodiment thereof, the molar weight of a surfactant is in the range of 300-800 g/mol. In a preferred embodiment thereof, the molar weight of a surfactant is in the range of 400-700 g/mol.

In an embodiment of the present invention the one or more surfactants is selected from the group consisting of zwitterionic surfactants, amphoteric surfactants, nonionic surfactants, cationic surfactants such as monovalent cationic surfactants, and mixtures thereof. In an embodiment of the present invention the one or more surfactants is selected from the group consisting of amphoteric surfactants, and nonionic surfactants, and mixtures thereof.

In an embodiment of the present invention, the one or more surfactants are selected from the group consisting of Marlipal® 24/939, Daclor 70-1-23, Stepanol WA-extra E, Lutensol TO 89, and combinations thereof. See further details herein below.

In an embodiment of the present invention, the one or more surfactants are selected from the group consisting of Marlipal® 24/939, Daclor 70-1-23, Stepanol WA-extra E, Lutensol TO 89, Ampholac 7TX, and combinations thereof.

In a specific embodiment of the present invention two of the one or more surfactants are Marlipal® 24/939 and Ampholac 7TX.

In a most preferred embodiment, the one or more surfactants comprised in a surfactant containing biocidal composition of the invention are selected from the group consisting of nonionic surfactants such as alkoxylated nonionic surfactants.

Liquid Carriers

In a preferred embodiment of the present invention, the one or more liquid carriers are selected from the group consisting of water, ethanol, glycerol, glycerine, propylene glycol and combinations thereof. See further details herein below.

Chelating Agents

In an embodiment of the present invention, the one or more chelating agents are selected from the group consisting of Masquol P320 Na, methylglycinediacetic acid (e.g. Trilon M), Potassium tripolyphosphate, and combinations thereof. In a more preferred embodiment, the one or more chelating agents is methylglycinediacetic acid (e.g. Trilon M) e.g. as the trisodium salt or other toxicological acceptable salts or solvates thereof. See further details herein below.

Detergent Builder

In an embodiment of the present invention, the one or more detergent builder are selected from the group consisting of Mackadet® 40K, soft soap, sodium citrate, and combinations thereof. In a more preferred embodiment of the detergent according to the invention, said detergent does not comprise a detergent builder as defined herein. See further details herein below.

Anionic Surfactants

The compositions of the invention may comprise an anionic surfactant. The compositions of the present invention may comprise a sulphonic acid surfactant, such as e.g., an alcohol ether sulphate sodium salt, e.g. $C_{12-13}$ alcohol ethylene glycol ether sulphate sodium salt (Daclor® 70-1-23 AL), or a linear alkyl benzene sulphonic acid or water-soluble salt forms thereof. Anionic surfactant(s) are typically present at a level of from 1.0% to 70%, preferably from 5.0% to 50% by weight, and more preferably from 10% to 30% by weight of the composition.

Anionic sulfonate or sulfonic acid surfactants suitable for use herein include the acid and salt forms of $C_{6-20}$, more preferably $C_{10-16}$, more preferably $C_{11-13}$ alkylbenzene sulfonates, $C_{6-20}$ alkyl ester sulfonates, $C_{6-22}$ primary or secondary alkane sulfonates, $C_{5-20}$ sulfonate polycarboxylic acids, and any mixtures thereof, but preferably $C_{11-13}$ alkylbenzene sulfonates.

Anionic sulphate salts or acids surfactants suitable for use in the compositions of the invention include the primary and secondary alkyl sulphates, having a linear or branched alkyl or alkenyl moiety having from 9 to 22 carbon atoms, preferably from 10 to 18 carbon atoms, and more preferably from 12 to 18 carbon atoms. In one embodiment of the composition according to the present invention one of the anionic surfactants are sodium lauryl sulfate (such as e.g. Stepanol® WA-Extra).

Also useful are beta-branched alkyl sulphate surfactants or mixtures of commercial available materials, having a weight average (of the surfactant or the mixture) branching degree of at least 50%. Mid-chain branched alkyl sulphates or sulfonates are also suitable anionic surfactants for use in the compositions of the invention. Preferred are the $C_{5-22}$, preferably $C_{10-20}$ mid-chain branched alkyl primary sulphates. When mixtures are used, a suitable average total number of carbon atoms for the alkyl moieties is preferably within the range of from greater than 14.5 to 17.5. Preferred mono-methyl-branched primary alkyl sulphates are selected from the group consisting of the 3-methyl to 13-methyl pentadecanol sulphates, the corresponding hexadecanol sulphates, and mixtures thereof. Dimethyl derivatives or other biodegradable alkyl sulphates having light branching can similarly be used.

Other suitable anionic surfactants for use herein include fatty methyl ester sulphonates and/or alkyl ethoxy sulphates (AES) and/or alkyl polyalkoxylated carboxylates (AEC). Mixtures of anionic surfactants can be used, for example mixtures of alkylbenzenesulphonates and AES.

The anionic surfactants are typically present in the form of their salts with alkanolamines or alkali metals such as sodium and potassium. Preferably, the anionic surfactants are neutralized with alkanolamines such as Mono Ethanol Amine or Triethanolamine, and are fully soluble in the liquid matrix of the compositions herein.

Amphoteric and Zwitterionic Surfactants

Suitable amphoteric or zwitterionic detersive surfactants for use in the composition herein include those which are known for use in hair care or other personal care cleansing. Non-limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from 8 to 18 carbon atoms and one contains an anionic group such as carboxy, sulfonate, sulfate, phosphate, or phosphonate. Suitable amphoteric detersive surfactants for use in the present invention include cocoamphoacetate, cocoamphodiacetate, lauroamphoacetate, lauroamphodiacetate, and mixtures thereof.

Zwitterionic detersive surfactants suitable for use in the compositions are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from 8 to 18 carbon atoms and one contains an anionic group such as carboxy, sulfonate, sulfate, phosphate or phosphonate. Zwitterionics such as betaines are suitable for use in this invention.

Furthermore, amine oxide surfactants having the formula: $R(EO)_{6x}(PO)_y(BO)_zN(O)(CH_2R')_2 \cdot qH_2O$ (I) are also suitable for incorporation within the compositions of the present invention. R is a relatively long-chain hydrocarbyl moiety which can be saturated or unsaturated, linear or branched, and can contain from 8 to 20, preferably from 10 to 16 carbon atoms, and is more preferably $C_{12-16}$ primary alkyl. R' is a short-chain moiety preferably selected from hydrogen, methyl and —$CH_2OH$. When x+y+z is different from 0, EO is ethyleneoxy, PO is propyleneneoxy and BO is butyleneoxy. Amine oxide surfactants are illustrated by $C_{12-14}$ alkyldimethyl amine oxide.

Non-limiting examples of other anionic, zwitterionic, amphoteric or optional additional surfactants suitable for use in the compositions are described in McCutcheon's, Emulsifiers and Detergents, 1989 Annual, published by M. C. Publishing Co., and in U.S. Pat. Nos. 3,929,678, 2,658,072; 2,438,091; 2,528,378. A preferred amphoteric surfactant is Ampholac 7TX™ also known as sodium talgamphopylycarboxyglycinate.

Nonionic Surfactants

In one embodiment of the present invention, the surfactant of formula I is a non-ionic surfactant.

The present compositions may also comprise, and preferably do comprise, this type of detersive surfactant. Essentially any alkoxylated nonionic surfactant, suitably ones containing only carbon, hydrogen and oxygen can be included in the present compositions, although amidofunctional and other heteroatom-functional types can in general also be used. Ethoxylated, propoxylated, butoxylated or mixed alkoxylated, for example ethoxylated/propoxylated aliphatic or aromatic hydrocarbyl chain nonionic surfactants are preferred. Suitable hydrocarbyl moieties can contain from 6 to 22 carbon atoms and can be linear, branched, cycloaliphatic or aromatic and the nonionic surfactant can be derived from a primary or secondary alcohol.

Preferred alkoxylated surfactants can be selected from the classes of the nonionic condensates of ethoxylated and ethoxylated/propoxylated or propoxylated/ethoxylated linear or lightly branched monohydric aliphatic alcohols, which can be natural or synthetic.

In a preferred embodiment, the one or more nonionic surfactants are selected from the group consisting of a $C_{12-14}$ alcohol polyethylene glycol ether mixture such as a mixture of fatty alcohols with 9 mol ethylene oxide and fatty alcohols with 3 mol ethylene oxide (e.g. Marlipal® 24/939); and iso-$C_{12-14}$ alcohol ethoxylates such as iso-$C_{13}$ alcohol ethoxylate (e.g. Lutensol TO 89) and combinations thereof.

In one preferred embodiment of the invention the composition comprises the nonionic ethoxylate as a linear alcohol ethoxylate, such as e.g. a $C_{12-14}$ alcohol polyethylene glycol ether mixture (e.g. CAS-NR 68439-50-9 comprised in Marlipal 24/939™ being a mixture of fatty alcohols with 9 mol ethylene oxide and fatty alcohols with 3 mol ethylene oxide) and combinations thereof. The average molar weight of CAS-NR 68439-50-9 comprised in Marlipal 24/939™ is about 447 g/mol.

In another preferred embodiment of the invention the composition comprises the nonionic ethoxylate which is selected from the group consisting of iso-alcohol ethoxylates such as iso-$C_{12-14}$ alcohol ethoxylates, such as preferably iso-$C_{13}$alcohol ethoxylate (e.g. CAS nr. 69011-36-5 comprised in Lutensol® TO) of the formula: $RO(CH_2CH_2O)_xH$, wherein R=iso-$C_{13}H_{27}$ and x=2, 3, 5, 6, 6.5, 7, 8, 10, 11, 12, 15, 20; and combinations thereof. More preferably Lutensol® TO 89, which has x=8. The molar weight of CAS nr. 69011-36-5 comprised in Lutensol® TO 89 is about 600 g/mol.

When R is $C_{18}$-alkyl, then the surfactant may not comprise an alkoxylated moiety that comprises higher alkoxides than the ethylene oxides, such as Plurafac® LF 300 comprising CAS nr. 69227-21-0, which is a low foaming nonionic surfactant. Plurafac® LF 300 is a C12-18 alcohol which is ethoxylated propoxylated. Accordingly, Plurafac® is not within the scope of above formula I.

Alkylphenyl alkoxylates such as the nonylphenyl ethoxylates can also suitably be used.

A preferred nonionic surfactant is Marlipal 24/939™. Another preferred nonionic surfactant is Lutensol TO 89.

Especially suitable as nonionic surfactant or co-surfactant are the condensation products of primary aliphatic alcohols with from 1 to 75 moles of $C_{2-3}$ alkylene oxide, more suitably 1 to 15 moles, preferably 1 to 11 moles. Particularly preferred are the condensation products of alcohols having an alkyl group containing from 8 to 20 carbon atoms with from 2 to 9 moles and in particular 3 or 5 moles, of ethylene oxide per mole of alcohol.

Suitable nonionic surfactants containing nitrogen as heteroatom include the polyhydroxy fatty amides having the structural formula $R^1CONRZ$, wherein $R^1$ is a $C_{5-31}$ hydrocarbyl, preferably straight-chain $C_{7-19}$ alkyl or alkenyl, more preferably straight-chain $C_{11-17}$ alkyl or alkenyl, or mixture thereof; $R^2$ is H, $C_{1-18}$, preferably $C_{1-4}$ hydrocarbyl, 2-hydroxethyl, 2-hydroxypropyl, ethoxy, propoxy, or a mixture thereof, preferably $C_{1-4}$ alkyl, more preferably methyl; and Z is a polyhydroxyhydrocarbyl having a linear hydrocarbyl chain with at least 3 hydroxyls directly connected to the chain. Z preferably will be derived from a reducing sugar such as glucose, a corresponding preferred compound being a $C_{11-17}$ alkyl N-methyl glucamide.

Other nonionic surfactants useful herein include the so-called "capped" nonionics in which one or more-OH moieties are replaced by —OR, wherein R is typically lower alkyl such as $C_{1-3}$ alkyl; the long-chain alkyl polysaccharides, more particularly the polyglycoside and/or oligosaccharide type, as well as nonionic surfactants derivable by esterifying fatty acids.

Cationic Nitrogen-Containing Detersive Surfactants

Cationic nitrogen-containing detersive surfactants suitable for use in the compositions of the present invention have at least one quaternized nitrogen and one long-chain hydrocarbyl group. Compounds comprising two, three or even four long-chain hydrocarbyl groups are also included. Examples of such cationic surfactants include alkyltrimethylammonium salts or their hydroxyalkyl substituted analogs, preferably compounds having the formula $R_1R_2R_3R_4N^+X^-$. $R_1$, $R_2$, $R_3$ and $R_4$ are independently selected from $C_{1-26}$ alkyl, alkenyl, hydroxyalkyl, benzyl, alkylbenzyl, alkenylbenzyl, benzylalkyl, benzylalkenyl and X is an anion. The hydrocarbyl groups $R_1$, $R_2$, $R_3$ and $R_4$ can independently be alkoxylated, preferably ethoxylated or propoxylated, more preferably ethoxylated with groups of the general formula $(C_2H_4O)_xH$ where x has a value from 1 to 15, preferably from 2 to 5. Not more than one of $R_2$, $R_3$ or $R_4$ should be benzyl. The hydrocarbyl groups $R_1$, $R_2$, $R_3$ and $R_4$ can independently comprise one or more, preferably two, ester- ([—O—C(O)—]; [—C(O)—O—]) and/or an amido-groups ([O—N(R)—]; [—N(R)—O—]), wherein R is defined as R1 above. The anion X may be selected from halide, methylsulfate, acetate and phosphate, preferably from halide and methylsulfate, more preferably from chloride and bromide. The $R_1$, $R_2$, $R_3$ and $R_4$ hydrocarbyl chains can be fully saturated or unsaturated with varying Iodine value, preferably with an Iodine value of from 0 to 140. At least 50% of each long chain alkyl or alkenyl group is predominantly linear, but also branched and/or cyclic groups are included.

For cationic surfactants comprising only one long hydrocarbyl chain, the preferred alkyl chain length for $R_1$ is $C_{12-15}$ and preferred groups for $R_2$, $R_3$ and $R_4$ are methyl and hydroxyethyl.

In a preferred embodiment, the cationic surfactants according to the invention are monovalent.

For cationic surfactants comprising two or three or even four long hydrocarbyl chains, the preferred overall chain length is $C_{18}$, though mixtures of chainlengths having non-zero proportions of lower, e.g., $C_{12}$, $C_{14}$, $C_{16}$ and some higher, e.g., $C_{20}$ chains can be quite desirable.

Preferred ester-containing surfactants have the general formula $\{(R_5)_2N((CH_2)_nER_6)_2\}^+X^-$, wherein each $R_5$ group is independently selected from $C_{1-4}$ alkyl, hydroxyalkyl or $C_{2-4}$ alkenyl; and wherein each $R_6$ is independently selected from $C_{8-28}$ alkyl or alkenyl groups; E is an ester moiety i.e., —OC(O)— or —C(O)O—, n is an integer from 0 to 5, and X is a suitable anion, for example chloride, methosulfate and mixtures thereof.

A second type of preferred ester-containing cationic surfactant can be represented by the formula: $\{(R_5)_3N(CH_2)_n CH(O(O)CR_6)CH_2O(O)CR_6\}^+X^-$, wherein $R_5$, $R_6$, X, and n are defined as above. This latter class can be exemplified by 1,2-bis[hardened tallowoyloxy]-3-trimethylammonium propane chloride.

The cationic surfactants, suitable for use in the compositions of the present invention can be either water-soluble, water-dispersable or water-insoluble.

Liquid Carriers

The compositions of the present invention may optionally comprise one or more liquid carriers. The liquid carrier can be aqueous or non-aqueous; and can include water alone or organic solvents alone and/or mixtures thereof. Preferred organic solvents include monohydric alcohols, dihydric alcohols, polyhydric alcohols, glycerol, glycols, glycerin, polyalkylene glycols, such as polyethylene glycol, and mixtures thereof.

In a more preferred embodiment of the present invention, the one or more liquid carriers are selected from the group consisting of water, ethanol, glycerol, propylene glycol, glycerine, and combinations thereof. In a more specific embodiment said one or more liquid carriers are propylene glycol and water and mixtures thereof.

Suitable monohydric alcohols especially include $C_{1-4}$ alcohols, such as ethanol, propanol, isopropanol and butanol. Preferred is 1,2-propanediol. Highly preferred on the organic solvent side are mixtures of solvents, especially mixtures of lower aliphatic alcohols such as ethanol, propanol, butanol, isopropanol, and/or diols such as 1,2-propanediol or 1,3-propanediol. The liquid carrier is typically present at levels in the range of from 1% to 95%, preferably from 5% to 70%, more preferably from 10% to 70%, even more preferably from 20% to 70%, yet even more preferably from 30% to 70%, and most preferably from 40% to 70% by weight of the composition.

A preferred combination of liquid carriers comprise water, ethanol and glycerol; for example in a ratio of about 16:1:3. Another liquid carrier system comprise water and glycerin; for example in a ratio of about 65:1, such as e.g. 60:1, 50:1, 40:1, 30:1 or 20:1. Alternatively a preferred liquid carrier is water.

A most preferred combination of liquid carriers comprises water and propylene glycol. In an embodiment of the invention, water and propylene glycol is comprised in a ratio of 10-18:0.5:1.5 by weight. In an embodiment of the invention, water and propylene glycol is comprised in a ratio of 12-16:0.8:1.2 by weight. In a preferred embodiment, water and propylene glycol is comprised in a ratio of about 14:1 by weight.

Detergent Builder

The compositions of the present invention may optionally comprise a builder, at levels of from 0.0% to 80% by weight, such as e.g. 1%, 5%, 10%, or 20%, preferably from 3% to 70% by weight, more preferably from 4% to 60% by weight of the composition. Preferably, the detergent according to the invention does not comprise a detergent builder.

In general any known detergent builder is useful herein, including inorganic types such as zeolites, layer silicates, fatty acids and phosphates such as the alkali metal polyphosphates, and organic types including especially the alkali metal salts of citrate (e.g. sodium citrate), 2,2-oxydisuccinate, carboxymethyloxysuccinate, nitrilotriacetate or the di- or trisodium salt thereof, and the like. Phosphate-free, water-soluble organic builders which have relatively low molecular weight, e.g., below 1,000, are highly preferred for use herein. Other suitable builders include sodium carbonate and sodium silicates having varying ratios of $SiO_2:Na_2O$ content, e.g., 1:1 to 3:1 with 2:1 ratio being typical.

Preferred are in particular saturated and/or unsaturated, linear and/or branched, fatty acids, such as medium-chain fatty acids ($C_{6-12}$) or long-chain fatty acids ($C_{12-18}$), and preferably mixtures of such fatty acids. In some instances of the present invention it is particular preferred to use $C_{12-18}$ saturated and/or unsaturated, linear and/or branched, fatty acids, and preferably mixtures of such fatty acids. Alternatively, or in combination, it may be preferred to use $C_{8-12}$ saturated and/or unsaturated, linear and/or branched, fatty acids, and preferably mixtures of such fatty acids, such as for example coconut fatty acids and salts thereof. Highly preferred have been found mixtures of saturated and unsaturated fatty acids, for example preferred is a mixture of rape seed-derived fatty acid and $C_{16-18}$ topped whole cut fatty acids, or a mixture of rape seed-derived fatty acid and a tallow alcohol derived fatty acid, coconut fatty acids, palmitic, oleic, fatty alkylsuccinic acids, soybean oil fatty acids, and mixtures thereof. Preferably potassium cocoate (Mackadet® 40-K) and/or soft soap. Further preferred are branched fatty acids of synthetic or natural origin, especially biodegradable branched types.

Mixtures of any of these fatty acid builders can be advantageous to further promote solubility. It is known that lower chain length fatty acids promote solubility but this needs to be balanced with the knowledge that they are often malodorous, e.g., at chain lengths of $C_9$ and below.

While the term "fatty acid builder" is in common use, it should be understood and appreciated that as formulated in the present detergents, the fatty acid may be in at least partially neutralized to neutralized form, the counter-ions can typically be alkanolamines, sodium, potassium, alkanolammonium or mixtures thereof. Preferably, the fatty acids are neutralized with alkanolamines such as Mono Ethanol Amine, and are fully soluble in the liquid phase.

Fatty acids may be builders in the compositions of the present invention. It has been found that the presence of fatty acid builders contribute to the formation of a coacervate. The presence of fatty acids builder in the compositions of the present invention is therefore preferred Suds Suppressor The compositions of the present invention may optionally comprise and preferably do comprise a suds suppressor. Suitable suds suppressors for use herein may comprise essentially any known antifoam compound or mixture, typically at a level less than 10%, preferably 0.001% to 10%, more preferably from 0.01% to 8%, most preferably from 0.05% to 5%, by weight of the composition. Suitable suds suppressors can include low solubility components such as highly crystalline waxes and/or hydrogenated fatty acids, silicones, silicone/silica mixtures, or more sophisticated compounded suds suppressor combinations, for example those commercially available from companies such as Dow Corning. Compounded silicones are suitably used at levels of 0.005% to 0.5% by weight. More soluble antifoams include for example the lower 2-alkyl alkanols such as 2-methyl-butanol.

Stabilizer

The compositions of the present invention may optionally comprise and preferably do comprise a stabilizer. Suitable levels of this component are in the range from 0.0% to 20%, preferably from 0.1% to 10%, and even more preferably from 0.1% to 3% by weight of the composition. The stabilizer serves to stabilize certain components of the compositions herein preventing them from coagulating and/or creaming.

Stabilizers suitable for use herein can be selected from thickening stabilizers. These include gums and other similar polysaccharides, for example gellan gum, carrageenan gum, and other known types of thickeners and rheological additives other than highly polyanionic types; thus conventional clays are not included.

More preferably the stabilizer is a crystalline, hydroxyl-containing stabilizing agent and/or hydrogenated jojoba, more preferably still, a trihydroxystearin, hydrogenated oil or a derivative thereof.

Chelating Agent

The compositions of the present invention may optionally comprise and preferably do comprise a chelating agent. Suitable chelating agents for use herein include nitrogen-containing, P-free aminocarboxylates, such as EDDS, EDTA and DTPA; aminophosphonates, such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelating agents, such as compounds of the general class of certain macrocyclic N-ligands, such as those known for use in bleach catalyst systems. Levels of chelating agents are typically lower than 6%, such as e.g. about 4-5%, or at levels of from 0.01% to 3%. In a preferred embodiment of the invention the chelating agent is selected from the group consisting of Aminotri(methylene phosponic acid)penta sodium salt (Masquol P320 Na™), Methylglycinediacetic acid, trisodium salt (e.g. Trilon® M), and potassium tripolyphosphate. More preferably selected from the group consisting of Aminotri(methylene phosponic acid) penta sodium salt (Masquol P320 Na™), and Methylglycinediacetic acid, trisodium salt (e.g. Trilon® M). In a more preferred embodiment, the one or more chelating agents is methylglycinediacetic acid (e.g. Trilon M) e.g. as the trisodium salt or other toxicological acceptable salts or solvates thereof.

Other Constituents

The laundry detergent according to the present invention may furthermore optionally comprise foam-stabilizers (e.g. amine oxides, for example cocoamine-N-oxide), anti-irritant agents, sequestering agent, brighteners, fragrances, dyes, dye-transfer inhibitors, pH adjusting agents (e.g. sodium citrate or triethanolamine), opacifiers, anti-oxidants, preservatives (e.g. Integra® 44) or combinations thereof.

For the purpose and intent of the present invention, the compositions of the present invention may typically have a pH ranging from pH 5.5 to pH 14, such as e.g., from pH 5.5 to pH 7, from pH 6 to pH 7, preferably between pH 6.0 and pH 11, more preferably between pH 6 and pH 8. Alternatively the pH may be in a range from between pH 7.5 and pH 11. In one preferred embodiment of the invention the pH is approximately neutral pH, about pH 7.

The laundry detergent according to the present invention may furthermore optionally comprise water soluble polymers, such as polymeric dispersing agents. Non-limiting examples thereof are for example copolymers of acrylic acid and sulfonated monomers, e.g. Alcosperse®240, for providing deposition control; or polymers of carboxylated and non-carboxylated monomers, e.g. Alcosperse 747, for providing detergens improvement.

The laundry detergent according to the present invention may furthermore optionally comprise fabric care ingredients, which are not fabric cleaning ingredients. In general, any fabric care ingredient known in the art of detergent composition may be used. However, certain fabric care ingredients are preferred, such as fabric care ingredients selected from the group consisting of clays, silicon-free amine compounds, silicon-free quaternary ammonium based compounds, nitrogen-free silicone polymers, amino silicone polymers, anionic silicone polymers, cationic silicone polymers, polyolefins, and mixtures thereof. In a preferred embodiment of the present invention where the delicate laundry detergent is to be used especially for washing textiles containing wool it is preferred that the composition comprises lanolin as a wool care additive. The Lanolin may for example be PEG 75/50 LV lanolin, and may preferably be present in an amount of about 0.5% to 5.0% by weight, such as 2.0%. In a preferred embodiment of the present invention where the delicate laundry detergent is to be used especially for washing textiles containing silk it is preferred that the composition comprises agent to maintain the silk textiles, such as for example Cosmacol® ESI, and may preferably be present in an amount of about 0.1% to 5.0% by weight, such as e.g. about 0.1% to 3%, 0.2% to 2%, 0.3% to 1%, preferably of about 0.5% by weight. When included in the compositions of the invention, suitable concentrations of fabric care ingredients are in general from 0.01% to 30%, preferably from 0.1% to 10%, and more preferably from 0.5% to 5.0% by weight of the composition.

The laundry detergent composition according to the present invention may furthermore optionally comprise a Cationic Deposition Aid, such as a Modified Cationic Deposition Aid. This is especially preferred when the compositions comprise one or more fabric care ingredients. The deposition aid is for enhancing the deposition rate and extend of e.g. an optional fabric care ingredient present. Typical levels of a deposition aid, if present, is in the range from 0.001% to 10%, preferably from 0.05% to 5.0%, more preferably from 0.1% to 2.5% by weight of the composition.

Preparation

The liquid laundry detergent compositions of the present invention can be prepared in any suitable manner and can, in general, involve any order of mixing or addition of the composition components, unless otherwise stated.

All patent and non-patent references cited in the application, or in the present application, are also hereby incorporated by reference in their entirety.

Items

A particular aspect of the invention relates to below items 1-28:

1. A laundry detergent composition comprising one or more biocides
2. The composition according to item 1, wherein the composition is a delicate laundry detergent composition.
3. The composition according to any of items 1 or 2, wherein the composition is a liquid laundry detergent.
4. The composition according to any of the preceding items, wherein the one or more biocides are selected from the group consisting of a PQ polymers; a polymeric biguanide polymer; an alkyl oxyethylene methyl ammonium salt; dialkyl oxyethylene methyl ammonium salt; povidone-iodine; an alkyl dimethyl benzyl ammonium salt; dialkyl methyl benzyl ammonium salt; a dialkyl dimethyl ammonium salt; and a bispyridine; or toxicological acceptable salts or solvates thereof.
5. The composition according to any of the previous items, wherein one of the one or more biocides is a polymeric biguanide polymer, or toxicological acceptable salts or solvates thereof.
6. The composition according to item 5, wherein the biocide is selected from the group consisting of PHMB, Poly(hexamethylenebiguanide) hydrochloride, Akacid Forte®, and Akacid®, or other toxicological acceptable salts or solvates thereof.
7. The composition according to any of the previous items, wherein one of the one or more biocides is an alkyl or dialkyl oxyethylene methyl ammonium salt.
8. The composition according to item 7, wherein the biocide is selected from the group consisting of N,N-didecyl-N-methyl-poly(oxyethyl) ammonium propionate (Bardap 26) and N,N-didecyl-N-methyl-poly(oxyethyl) ammonium lactate.
9. The composition according to any of the previous items, wherein one of the one or more biocides is povidone-iodine.
10. The composition according to any of the previous items, wherein one of the one or more biocides is an alkyl dimethyl benzyl ammonium salt or a dialkyl methyl benzyl ammonium salt.
11. The composition according to item 10, wherein the biocide is selected from the group consisting of Coco benzyl dimethyl ammonium chlorides with predominantly $C_{12-14}$alkyl; dicoco benzyl methyl ammonium chlorides with predominantly $C_{12-14}$alkyl; benzyl $C_{12-18}$-alkyldimethyl ammonium chlorides; benzyl $C_{12-14}$-alkyldimethyl ammonium chlorides, and $C_{12-13}$-alkyl[(ethylphenyl)methyl]dimethyl ammonium chlorides (ADBAC).
12. The composition according to item 10, wherein the biocide is $C_{12-13}$-alkyl[(ethylphenyl)methyl]dimethyl ammonium chlorides (ADBAC).
13. The composition according to any of the previous items, wherein one of the one or more biocides is a dialkyl dimethyl ammonium salt.
14. The composition according to item 13, wherein the biocide is selected from the group consisting of didecyl dimethyl ammonium chloride, dioctyl dimethyl ammonium chloride, and octyl decyl dimethyl ammonium chloride (DDAC).
15. The composition according to any of the previous items, wherein one of the one or more biocides is a bispyridine, or toxicological acceptable salts or solvates thereof.
16. The composition according to item 15, wherein the biocide is Octenidine dihydrochloride.
17. The composition according to any of the previous items, wherein one of the one or more biocides is a PQ polymer, or toxicological acceptable salts or solvates thereof.
18. The composition according to item 17, wherein the biocide is N,N-Dimethyl-2-hydroxypropylammonium chloride polymer.
19. The composition according to any of items 1-4, wherein the one or more biocides is a mixture of Akacid Forte® and Bardap-26.
20. The composition according to any of the previous items, wherein the composition do not comprise enzymes.
21. The composition according to any of the previous items, wherein the composition is suitable for washing at low temperatures in a range of 5° C. to 40° C.
22. The composition according to any of the previous items, wherein the delicate laundry detergent further comprises
    i) one or more surfactants;
    ii) one or more liquid carriers;
    iii) one or more chelating agents; and
    iv) one or more detergent builders.
23. The composition according to item 22, wherein the one or more surfactants are selected from the group consisting of zwitterionic surfactants, amphoteric surfactants, nonionic surfactants, cationic surfactants, and mixtures thereof.
24. The composition according to any of items 22 or 23, wherein the one or more surfactants are selected from the group consisting of Marlipal® 24/939, Daclor 70-1-23, Stepanol WA-extra E, Lutensol TO 89, Plurafac LF 300, Ampholac 7TX, and combinations thereof.
25. The composition according to any of items 22-24, wherein the one or more liquid carriers are selected from the group consisting of water, ethanol, glycerol, glycerine, and combinations thereof.
26. The composition according to any of items 22-25, wherein the one or more chelating agents are selected from the group consisting of Masquol P320 Na, Trilon M, Potassium tripolyphosphate, and combinations thereof.
27. The composition according to any of items 22-26, wherein the one or more detergent builder are selected from the group consisting of Mackadet® 40K, soft soap, sodium citrate, and combinations thereof.
28. The composition according to any of the previous items, wherein the composition is for washing of clothing or textiles considered to be a source of infection, e.g. hospital laundry or nursing home laundry.

FIGURES

Figure 2:
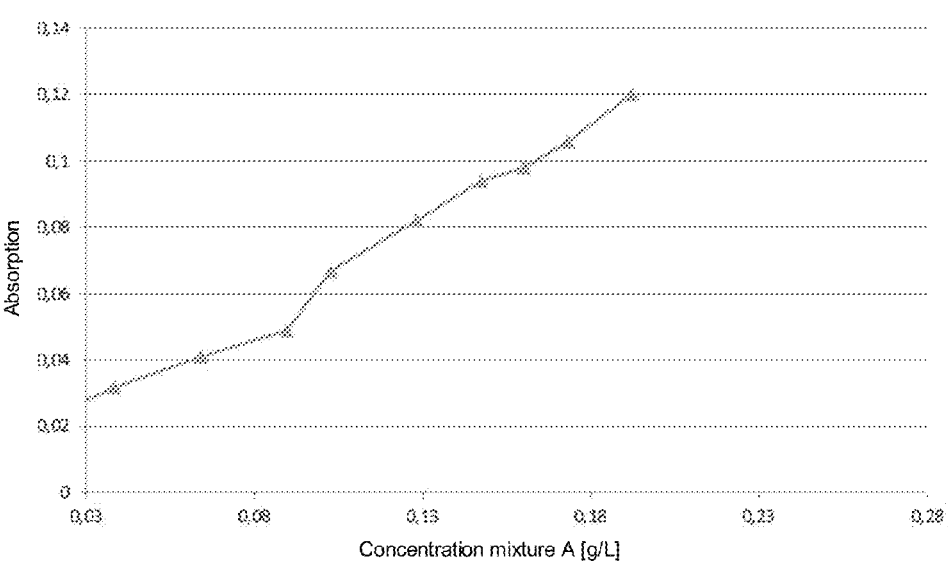

FIGS. 1 and 2 display the CMC absorption data obtained for diluted Detergent A (table 8a)

Figure 3:
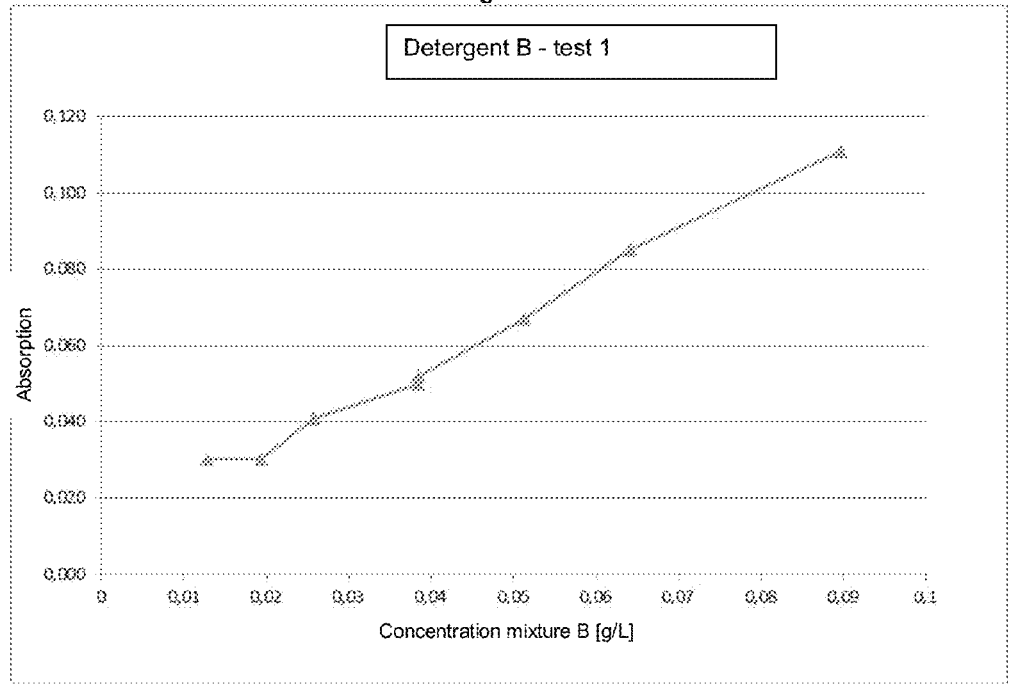
Figure 4:
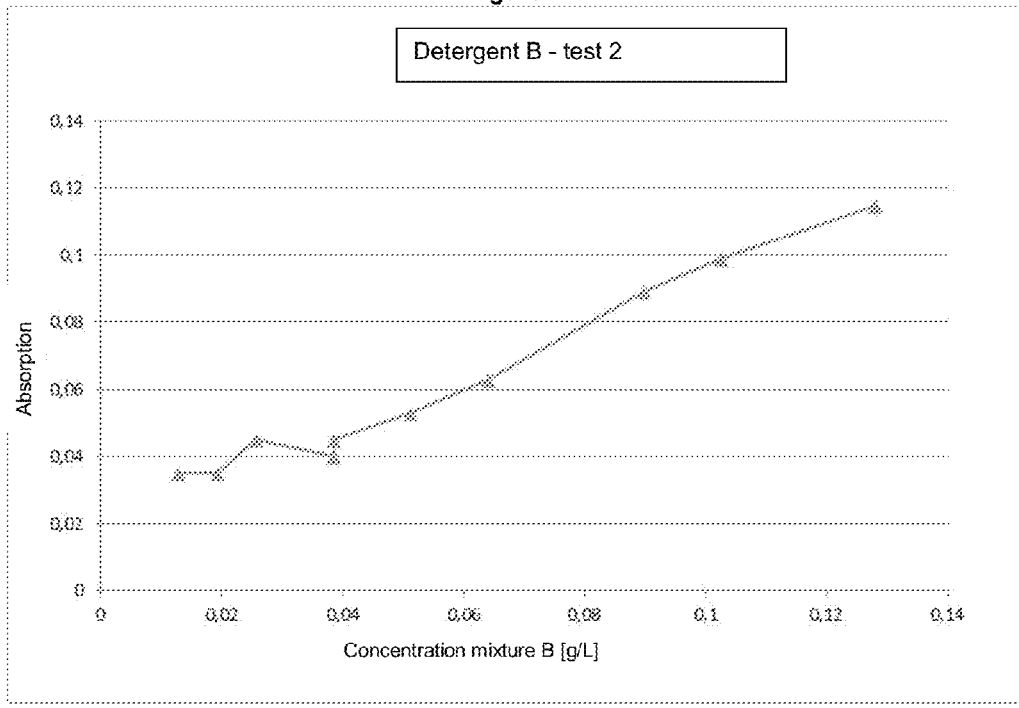

FIGS. 3 and 4 display the CMC absorption data obtained for diluted Detergent B (table 8c)

Figure 5:
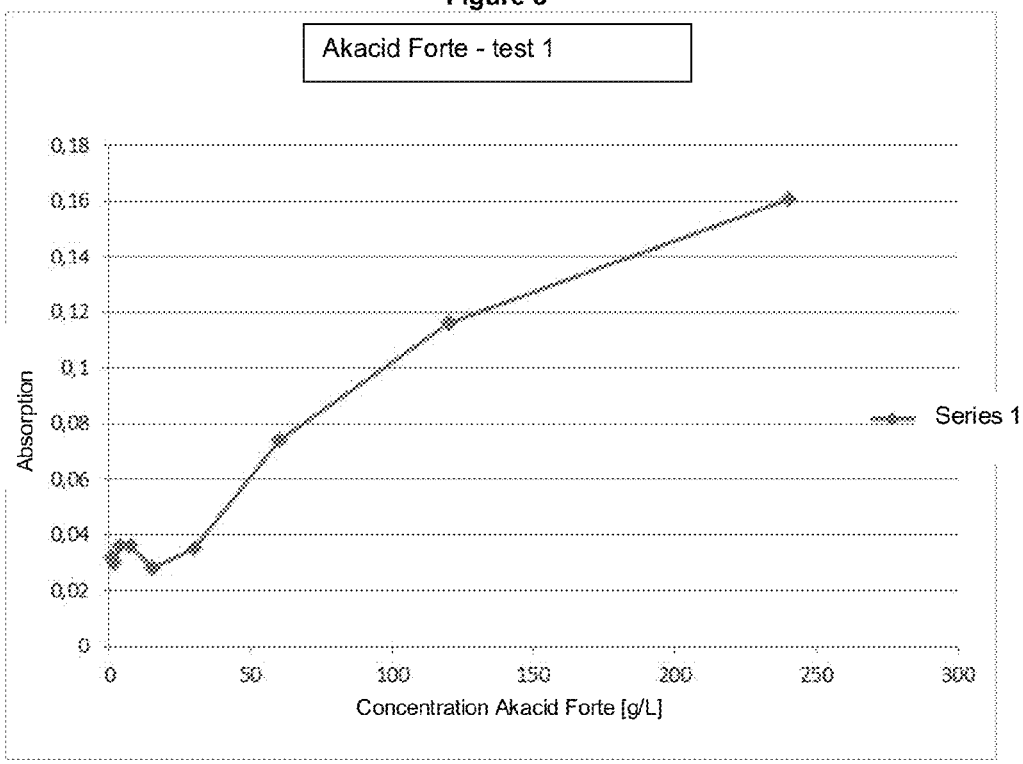
Figure 6:
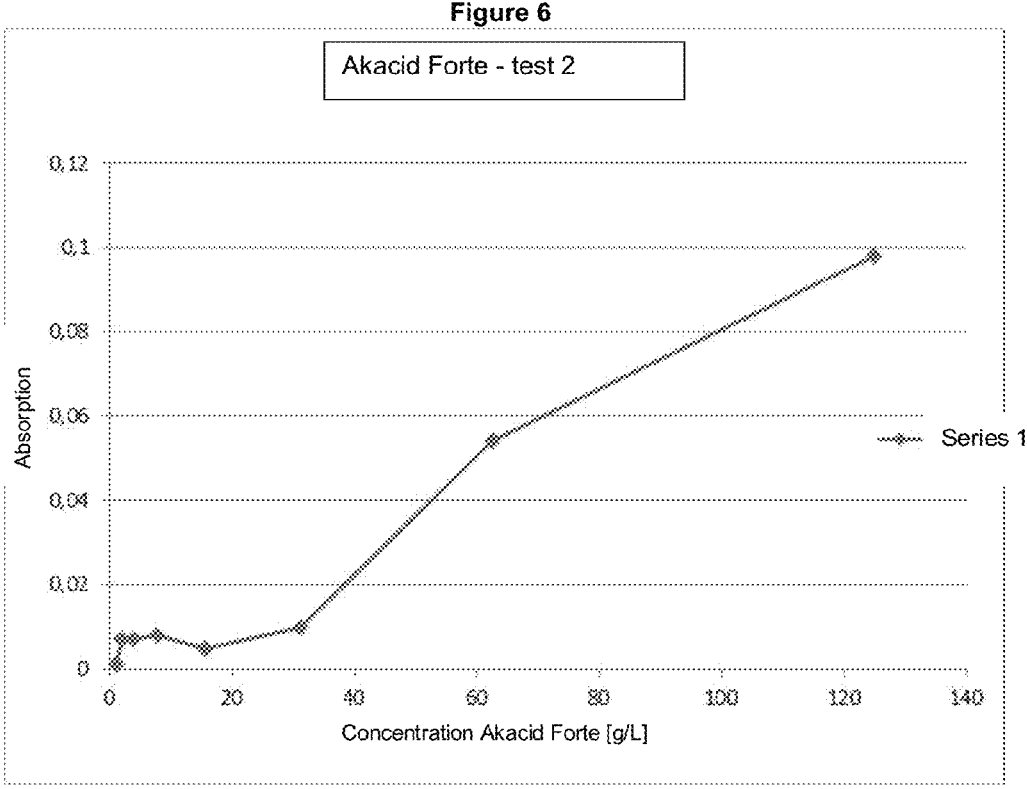

FIGS. 5 and 6 display the CMC absorption data obtained for diluted Akacid Forte

EXAMPLES

The following non-limiting examples are illustrative of the present invention. Percentages are by weight unless otherwise specified.

Example 1

Delicate Liquid Laundry Detergent for Wool and Fine Textiles

The below table provides a detergent composition to be combined with one or more biocides as described herein. This particular detergent composition is preferably for washing wool, and may be used for other fine textiles.

| Ingredient | Amount (% by weight) |
| --- | --- |
| Marlipal 24/939 | 25.0% |
| Mackadet 40K | 5.0% |
| Sodium Citrate | 10.0% |
| Masquol P320 Na | 4-5% |
| Alcoperse 240 | 1-2% |
| Alcoperse 747 | 1-2% |
| Lanolin, PEG-75/50 LV | 2% |
| MGP, Glycerol | 7.5% |
| Ethanol | 2.5% |
| Water | Up to 100% |

Example 2

Delicate Liquid Laundry Detergent for Silk and Fine Textiles

The below table provides a detergent composition to be combined with one or more biocides as described herein. This particular detergent composition is preferably for washing silk, and may be used for other fine textiles.

| Ingredient | Amount (% by weight) |
| --- | --- |
| Daclor 70-1-23 | 10.3% |
| Stepanol WA-extra E | 16.7% |
| Mackadet 40K | 1.0% |
| Marlipal 24/939 | 3.4% |
| Cosmacol ESI | 0.5% |
| Integra 44 | 0.3% |
| opacifier | q.s. |
| Perfume | q.s. |
| Water | Up to 100% |

Example 3

Liquid Laundry for Textiles

The below table provides a detergent composition to be combined with one or more biocides as described herein. This particular detergent composition is for washing textiles in general and may be used for fine textiles.

| Ingredient | Amount (% by weight) |
| --- | --- |
| Soft soap | 10-20% |
| Sodium lauryl sulphate | 5-10% |
| Triton M (MGDA) | 0.5-2.0% |
| Potassium tripolyphosphate | 5-10% |
| Lutensol TO 89 | 5-10% |
| Plurafac LF300 | 1-3% |
| Glycerine | 1-3% |
| Perfume and colour | q.s. |
| Water | 60-65% |

Example 4

Assay for Biocidal Effect

The one or more biocides are assayed for in vitro biocidal effect. There may either be assayed one biocide alone or two or more biocides in combination. Five different concentrations of the one or more biocides may be assayed at e.g. two different temperatures in the range of 20-40° C. The exposure time of biocide to microorganism may be selected to represent the desired washing process for the laundry detergent composition in question. For example 1 hour for a delicate laundry detergent suitable for wool or silk wash, or 2 hours for a laundry detergent suitable for heavy-duty wash of e.g. hospital textiles.

The one or more biocide may be assayed against the following microorganisms: *Escherichia coli*, *Staphylococcus aureus*, *Pseudomonas aeruginosa*, and *Candida albicans*. *Escherichia coli* have been chosen in order to represent a gram negative faecal bacteria; *Staphylococcus aureus* have been chosen in order to represent a gram positive, heat tolerant bacteria; *Pseudomonas aeruginosa* have been chosen in order to represent a disease causing bacteria that in some cases are difficult to treat; and *Candida albicans* represent the presence of fungi.

The reduction in the different microorganisms is quantified. This assay may be used to determine the biocidal effect of one specific biocide, or a combination of biocides. The later determining whether a synergistically effect is obtained.

Example 4A

Biocidal Effect

Dosage Response

The assay is based on the requirements to chemical disinfectants and antiseptic agent with regard to a reduction in fungus and bacteria of 4 and 5 log units respectively. These requirements are stated in DS/EN 1276:1997 and DS/EN 1275:2005, respectively.

Microorganisms and Stock Cultures

The following microorganisms were chosen for this dosage response assays: *Staphylococcus aureus*, ATCC 6538, representing grampositive bacteria; *Escherichia coli*, ATCC 11229, representing gramnegative bacteria; and *Candida albicans*, ATCC 2091, representing yeast fungi.

The bacterial cultures were cultivated in the growth medium TSB (Tryptic Soy Bouillon) for 24 h at 37° C. before use. Colony forming units (CFU) were determined by plating Tryptic Soy Agar (TSA).

*Candida albicans* was cultivated on malt extract agar (MEA) for 24 h at 37° C. before use. Then the yeast cells were harvested in 0.9% saline by use of a drigalski spatula. CFU were determined by plating on MEA.

The above described cultures are termed the stock cultures.

Biocides

The biocides and concentrations assayed can be seen in Table 1.

TABLE 1

Test concentrations of biocides

| Biocide (% active) | Test concentrations** | | | | | |
|---|---|---|---|---|---|---|
| | 700 ppm active | 200 ppm active | 160 ppm active | 120 ppm active | 80 ppm active | 40 ppm active |
| Akacid (25%) CAS 37457-91-5 | 2800 ppm | 800 ppm | 640 ppm | 480 ppm | 320 ppm | 160 ppm |
| Akacid Forte (25%) CAS 57028-96-3 | 2800 ppm | 800 ppm | 640 ppm | 480 ppm | 320 ppm | 160 ppm |
| Akacid Plus * (25%) CAS 37457-91-5 CAS 57028-96-3 | 2800 ppm | 800 ppm | 640 ppm | 480 ppm | 320 ppm | 160 ppm |
| Lonzabac BG (20%) CAS 27083-27-8 | 3500 ppm | 1000 ppm | 800 ppm | 600 ppm | 400 ppm | 200 ppm |
| Bardap-26 (70%) CAS 94667-33-1 | 1000 ppm | 286 ppm | 229 ppm | 171 ppm | 114 ppm | 57 ppm |
| Barquat PQ-2 (50%) CAS 25988-97-0 | 1400 ppm | 400 ppm | 320 ppm | 240 ppm | 160 ppm | 80 ppm |

* Akacid Plus is a mixture of Akacid and Akacid Forte in a 1:1 ratio.
**The test solutions were prepared in aqueous solutions in a concentration corresponding to 10 times the desired. (ppm = mg per kg/liter)

Exposure to Biocide

The exposure to biocide was performed at pH 6-6.5, which was obtained by addition of 100 mM potassium phosphate buffer. To test tubes with 8 mL sterile 100 mM phosphate buffer were added 1 mL test solution (i.e. biocide solution) and 1 mL stock culture. After thorough mixing the assay mixtures were exposed to heating in water bath at 30° C. for 9 minutes. After exposure the test tubes were immediately removed from the water bath and the surviving microorganisms were determined by plating.

Reference samples were prepared by adding 1 mL sterile water instead of 1 mL test solution.

Plating on Agar

From appropriate dilutions of starting material (mixture of biocide solution, stock culture and buffer) was taken 0.1 mL onto agar plates, and the material was spread with Drigalski spatulas. The plates were incubated at 37° C. 1 day for bacteria and 2 days for yeast.

For determining CFU of the bacteria after exposure, with and without biocide, was used incubation on TSA for 24 h at 37° C. For determining CFU of *Candida albicans* before and after exposure was used incubation on MEA for 48 h at 37° C.

Where a large reduction in organisms was expected (test concentrations of 700 and 200 ppm) 1 mL and 0.1 mL solution, respectively, were mixed with 100 ml sterile water and filtered through a 47 mm Millipore EZ-Pak® membrane filter, mesh 0.22 μm. The filter was rinsed with 100 mL sterile water, and thereafter placed directly on the agar plate. The mixing in water and subsequent rinsing ensures that the biocide is heavily diluted and thus will not have any effect after plating. For dilutions of 100× and more, regular plating were used, as the biocide at these concentrations is considered to not provide any further reduction in the microorganisms during plating on agar.

Plates with between 20 and 500 CFU were chosen for counting. Number of CFU (colony forming units) per g or mL sample was calculated by multiplying the number of colonies per plate with the dilution and further by 10, as only 0.1 mL was used on each plate.

After incubation, CFU was determined and reduction in organisms was calculated. All tests were performed in triplicate.

Results

In relation to *E. Coli*, see Table 2, especially Bardap-26 and Akacid Forte showed a good effect. The counting gave a reduction in organisms of $>10^7$ for Bardap in a concentration of 160 ppm. The effect was smaller for Akacid Forte where the reduction in organisms only was $>10^5$. The remaining biocides showed no or limited effect.

Barquat PC-2 showed no effect, and may be used as a negative control. These findings show the importance of choosing the appropriate biocide for the intended microorganism.

TABLE 2

Reduction obtained in *E. coli*

| Biocide (% active) | Test concentrations** | | | | | |
|---|---|---|---|---|---|---|
| | 700 ppm active C1 | 200 ppm active C2 | 160 ppm active C3 | 120 ppm active C4 | 80 ppm active C5 | 40 ppm active C6 |
| Akacid (25%) CAS 37457-91-5 | ~$10^6$ | $10^2$-$10^3$ | No reduction | | | |

TABLE 2-continued

Reduction obtained in *E. coli*

| Biocide (% active) | Test concentrations** | | | | | |
|---|---|---|---|---|---|---|
| | 700 ppm active C1 | 200 ppm active C2 | 160 ppm active C3 | 120 ppm active C4 | 80 ppm active C5 | 40 ppm active C6 |
| Akacid Forte (25%) CAS 57028-96-3 | $>10^7$ | $\sim 10^5$ | $\sim 10^5$ | $\sim 10^3$ | $10^2$-$10^3$ | No reduction |
| Akacid Plus * (25%) CAS 37457-91-5 CAS 57028-96-3 | $>10^7$ | $10^3$-$10^4$ | $10^2$-$10^3$ | No reduction | | |
| Lonzabac BG (20%) CAS 27083-27-8 | $>10^7$ | $10^3$-$10^4$ | $10^2$-$10^3$ | No reduction | | |
| Bardap-26 (70%) CAS 94667-33-1 | $>10^7$ | $>10^7$ | $>10^7$ | $10^4$-$10^5$ | $\sim 10^4$ | $\sim 10^4$ |
| Barquat PQ-2 (50%) CAS 25988-97-0 | No reduction | | | | | |

* Akacid Plus is a mixture of Akacid and Akacid Forte in a 1:1 ratio.
** The test solutions were prepared in aqueous solutions in a concentration corresponding to 10 times the desired. (ppm = mg per kg/liter)

In relation to *Staphylococcus Aureus*, see Table 3, especially Bardap-26 at 160 ppm and in part Akacid Forte showed a good effect, while the remaining biocides showed no or very limited effect. Bardap-26 reduced *Staphylococcus Aureus* by $>10^7$ at 160 ppm. Akacid Forte reduced by $>10^4$. Barquat PQ-2 showed no effect, and may be used as a negative control. These findings again show the importance of choosing the appropriate biocide for the intended microorganism.

TABLE 3

Reduction obtained in *Staphylococcus Aureus*

| Biocide (% active) | Test concentrations** | | | | | |
|---|---|---|---|---|---|---|
| | 700 ppm active C1 | 200 ppm active C2 | 160 ppm active C3 | 120 ppm active C4 | 80 ppm active C5 | 40 ppm active C6 |
| Akacid (25%) CAS 37457-91-5 | $>10^8$ | $<10^5$ | $<10^5$ | $\sim 10$ | No reduction | |
| Akacid Forte (25%) CAS 57028-96-3 | $>10^6$ | $10^5$-$10^4$ | $\sim 10^4$ | No reduction | | |
| Akacid Plus * (25%) CAS 37457-91-5 CAS 57028-96-3 | $>10^7$ | $\sim 10^2$ | No reduction | | | |
| Lonzabac BG (20%) CAS 27083-27-8 | $>10^7$ | $10^5$-$10^4$ | $10^5$-$10^4$ | $10^2$-$10^3$ | $10^2$-$10^3$ | $\sim 10$ |
| Bardap-26 (70%) CAS 94667-33-1 | $>10^7$ | $>10^7$ | $>10^7$ | $10^2$-$10^3$ | $10^2$-$10^3$ | $\sim 10^2$ |
| Barquat PQ-2 (50%) CAS 25988-97-0 | $<10^5$ | No reduction | | | | |

* Akacid Plus is a mixture of Akacid and Akacid Forte in a 1:1 ratio.
** The test solutions were prepared in aqueous solutions in a concentration corresponding to 10 times the desired. (ppm = mg per kg/liter)

In relation to *Candida Albicans*, see Table 4, especially Bardap-26 showed a good effect, while the remaining biocides showed no or very limited effect. Bardap-26 reduced *Candida Albicans* by $10^4$. Barquat PQ-2 showed no effect, and may be used as a negative control. These findings again show the importance of choosing the appropriate biocide for the intended microorganism.

TABLE 4

Reduction obtained in *Candida Albicans*

| Biocide (% active) | Test concentrations** | | | | | |
|---|---|---|---|---|---|---|
| | 700 ppm active C1 | 200 ppm active C2 | 160 ppm active C3 | 120 ppm active C4 | 80 ppm active C5 | 40 ppm active C6 |
| Akacid (25%) CAS 37457-91-5 | ~$10^4$ | ~10 | No reduction | | | |
| Akacid Forte (25%) CAS 57028-96-3 | ~$10^4$ | | No reduction | | | |
| Akacid Plus * (25%) CAS 37457-91-5 CAS 57028-96-3 | ~$10^4$ | ~10 | No reduction | | | |
| Lonzabac BG (20%) CAS 27083-27-8 | ~$10^4$ | | No reduction | | | ~10 |
| Bardap-26 (70%) CAS 94667-33-1 | $10^4$-$10^5$ | ~$10^4$ | ~$10^4$ | ~$10^3$ | $10^2$-$10^3$ | No reduction |
| Barquat PQ-2 (50%) CAS 25988-97-0 | ~$10^4$ | | No reduction | | | |

Example 4B

Biocidal Effect

Synergistical Effect

The optimal biocides, Bardap-26 and Akacid Forte, found in Example 4A, were further assayed for synergistically effect. Bardap-26 and Akacid Forte was mixed in a 50:50 ratio, and the applied concentrations can be seen from Table 5. The methods and solutions were otherwise as described in example 4A herein.

TABLE 5

Test concentrations of 50:50 mixtures of Bardap-26 and Akacid Forte

| Biocide (% active) | Test concentrations | | | | | |
|---|---|---|---|---|---|---|
| | 700 ppm active | 200 ppm active | 160 ppm active | 120 ppm active | 80 ppm active | 40 ppm active |
| Bardap-26 (70%) CAS 94667-33-1 + Akacid Forte (25%) CAS 57028-96-3 | 500 ppm + 1400 ppm | 143 ppm + 400 ppm | 114 ppm + 320 ppm | 86 ppm + 240 ppm | 57 ppm + 160 ppm | 29 ppm + 80 ppm |

TABLE 6

Reductions obtained in three organisms by use of 50:50 mixture of Bardap-26 and Akacid Forte

| Organism | Test concentrations/Reduction obtained | | | | | |
|---|---|---|---|---|---|---|
| | 700 ppm active | 200 ppm active | 160 ppm active | 120 ppm active | 80 ppm active | 40 ppm active |
| E. coli | >$10^7$ | >$10^7$ | >$10^6$ | >$10^6$ | >$10^6$ | >$10^6$ |
| Staphylococcus aureus | >$10^7$ | >$10^7$ | >$10^6$ | >$10^6$ | ~$10^5$ | ~$10^3$ |
| Candida albicans | >$10^7$ | >$10^7$ | >$10^7$ | >$10^6$ | ~$10^3$ | No effect |

Gray indicates high effect.

Results

As can be seen from Table 6, there was found a clear and surprising synergistical effect for all of the assayed organisms. The synergistical effect was especially evident for *E. coli*, as there was found a total elimination. For *Staphylococcus Aureus* and *Candida Albicans* were likewise found a synergistical effect, as the combination gave a significant increase in reduction compared to the effects previously observed for either biocide alone.

Example 5

Assay for Washing and Biocidal Effect

The microorganisms, as mentioned in example 4, are inoculated on the textile in question. For a delicate laundry detergent the textile is wool and/or silk, and for a detergent composition for heavy-laundry duty the textile may be cotton, a cotton containing textile, a polyester containing textile etc.

The inoculated textile is washed by standardises methods with the laundry detergent to be assayed. The wash is performed at different temperatures, concentrations, and under conditions suitable for the intended use of the laundry detergent composition.

The reduction in the different microorganisms is quantified.

This assay is used to determine the biocidal effect of the laundry detergent under washing conditions.

Example 6

Liquid Laundry Detergent for Fine Textiles

The below table provides a liquid laundry detergent composition for fine textiles, i.e. a delicate laundry detergent, to be combined with one or more biocides as described herein; preferably Bardap-26 or Akacid Forte, or a mixture thereof.

TABLE 7

Test concentrations of biocides

| Ingredient | Amount (in g pr. Kg) |
|---|---|
| Marlipal 24/939 | 250 g |
| Ampholac | 200 g |
| Trilon M | 30 g |
| Propyleneglycol | 50 g |
| Water | 470 g |

The liquid laundry may be prepared by adding the components to the specified amount of water and stirring after addition of each component. Thereafter the pH is adjusted to pH 6.0-6.5.

Example 7

Liquid Laundry Detergent for Fine Textiles

The exemplified liquid laundry detergents for fine textiles, i.e. delicate laundry detergents, comprise:
- one or more chelating agents such as but not limited to Trilon M,
- one or more non-ionic surfactants or monovalent cationic surfactants such as but not limited to the surfactants selected from the group consisting of Lutensol TO 89 and Marlipal 24/93
- one or more liquid carriers such as but not limited to water and propylene glycol
- optionally one or more biocides such as but not limited to biocides selected from the group consisting of Bardap-26 and Akacid Forte.

Below detergents A, B and C were prepared with and without biocides (Tables 8a-f):

TABLE 8a

Detergent A with biocides

| Ingredient | Amount % (w/w) |
|---|---|
| Water | 69.5 |
| Propylene glycol | 5 |
| Trilon ® M | 3 |

TABLE 8a-continued

Detergent A with biocides

| Ingredient | Amount % (w/w) |
|---|---|
| Lutensol TO 89 (90% (w/w) isotridecanolethoxylat, polymer (CAS nr. 69011-36-5)) | 12.5 |
| Bardap-26 comprising 70% CAS 94667-33-1 * | 5 |
| Akacid Forte comprising 25% CAS 57028-96-3 ** | 5 |

TABLE 8b

Detergent A without biocides

| Ingredient | Amount % (w/w) |
|---|---|
| Water | 79.5 |
| Propylene glycol | 5 |
| Trilon ® M | 3 |
| Lutensol TO 89 (90% (w/w) isotridecanolethoxylat, polymer (CAS nr. 69011-36-5)) | 12.5 |

TABLE 8c

Detergent B with biocides

| Ingredient | Amount % (w/w) |
|---|---|
| Water | 69.5 |
| Propylene glycol | 5 |
| Trilon M | 3 |
| Marlipal 24/939 (90% CAS-NR 68439-50-9 (w/w)) | 12.5 |
| Bardap-26 comprising 70% CAS 94667-33-1 * | 5 |
| Akacid Forte comprising 25% CAS 57028-96-3 ** | 5 |

TABLE 8d

Detergent B without biocides

| Ingredient | Amount % (w/w) |
|---|---|
| Water | 79.5 |
| Propylene glycol | 5 |
| Trilon M | 3 |
| Marlipal 24/939 (90% CAS-NR 68439-50-9 (w/w)) | 12.5 |

TABLE 8e

Detergent C with biocides

| Ingredient | Amount % (w/w) |
|---|---|
| Water | 69.5 |
| Propylene glycol | 5 |
| Trilon ® M | 3 |
| Plurafac LF 300 (90% (w/w) CAS nr. 69227-21-0)) | 12.5 |
| Bardap-26 comprising 70% CAS 94667-33-1 * | 5 |
| Akacid Forte comprising 25% CAS 57028-96-3 ** | 5 |

TABLE 8f

Detergent C without biocides

| Ingredient | Amount % (w/w) |
| --- | --- |
| Water | 79.5 |
| Propylene glycol | 5 |
| Trilon ® M | 3 |
| Plurafac LF 300 (90% (w/w) CAS nr. 69227-21-0)) | 12.5 |

Liquid laundry detergents A, B and C with and without biocides may be prepared by adding the components to the specified amount of water and stirring after addition of each component. Thereafter the pH is adjusted to pH 6-7 using e.g. lactic acid.

* A content of 5% (w/w) Bardap-26 comprising 70% CAS 94667-33-1 in each of detergents A, B and C gives a content of 3.5% (w/w) CAS 94667-33-1, which is the active ingredient in Bardap-26.

** A content of 5% (w/w) Akacid Forte comprising 25% CAS 57028-96-3 in each of detergents A, B and C gives a content of 1.25% (w/w) CAS 57028-96-3, which is the active ingredient in Akacid Forte.

The stability of liquid laundry detergents A, B and C with comprising 5% (w/w) Bardap-26 and 5% (w/w) Akacid Forte were analyzed after 1 week storage at −18° C., 5° C., 20° C. and 58° C.:

TABLE 9

Results obtained in stability test

| Storage temperature | −18° C. | 5° C. | 20° C. | 58° C. |
| --- | --- | --- | --- | --- |
| Detergent A | stable | stable | stable | stable |
| Detergent B | stable | stable | stable | stable |
| Detergent C | stable | stable | stable | stable |

Detergent C without biocides is the only detergent of detergents A without biocides, B without biocides and C without biocides which was not stable.

Conclusion

No precipitate occurred in detergent A with biocides upon storage for 1 week at −18° C.-58° C. No precipitate occurred in composition B with biocides upon storage for 1 week at −18° C.-58° C. No precipitate occurred in composition C with biocides upon storage for 1 week at −18° C.-58° C. In conclusion, liquid laundry detergents A, B and C are stable. Detergent C without biocides is not stable.

Example 8

Biocidal Effect of Detergent and Detergent with Biocides
Bacteria and Yeast Stock Cultures

*Staphylococcus aureus*, ATCC 6538 representing Gram-positive bacteria.

*Escherichia coli*, ATCC 11229 representing Gram-negative bacteria.

*Candida albicans*, ATCC 2091 representing yeasts.

Bacteria were cultivated in TSB (Tryptic Soy Bouillon) at 37° C. for 24 hours. This culture was designated bacterial stock culture.

*Candida albicans* was cultivated on MEA (Malt extract Agar) at 37° C. for 24 hours. The yeast was harvested by adding 10 mL 0.9% NaCl per plate and the yeast loosened with a Drigalski spatula. The yeast suspension was collected in a jar with glass beads and whirled to ensure an even distribution of the cells. This culture was designated yeast stock culture. Counts of yeast CFU after exposure was carried out using normal plate counts on MEA at 37° C. for 48 hours.

Biocide Stock Solution

A 12000 ppm biocides stock solution comprising 6000 ppm of the active ingredient in Akacid Forte (CAS 57028-96-3)+6000 ppm of the active ingredient in Bardap-26 (CAS 94667-33-1) was made in potassium phosphate buffer, pH 6.0.

Test Solution 1

Test solution 1 was prepared by addition of 0.5 ml biocides stock solution and 8.5 ml potassium phosphate buffer to sterile test tubes. Test solution 1 comprises no detergent.

Test Solution 2

Test solution 2 was prepared by addition of 1.0 ml biocides stock solution and 8 ml potassium phosphate buffer to sterile test tubes. Test solution 2 comprises no detergent.

Prior to use in test solutions 3-8, detergent solutions A and B with and without biocides were made in accordance with Example 7 and pH was adjusted to 6.0-6.5 by adding of 1M NaOH.

Test Solution 3

Detergent A without biocides (table 8b) was diluted with water to a concentration of 5.4 g/liter test solution:

Detergent A comprises 11.25% (w/w) of the active ingredient in Lutensol TO 89 (CAS nr. 69011-36-5). Thereby test solution 3 comprises CAS nr. 69011-36-5 in an amount of 0.61 g/liter test solution.

Test solution 3 comprises no biocide.

Test Solution 4

Detergent A with biocides (table 8a) was diluted with water to a concentration of 6 g/900 ml test solution:

Detergent A comprises 11.25% (w/w) of the active ingredient in Lutensol TO 89 (CAS nr. 69011-36-5). Thereby test solution 4 comprises CAS nr. 69011-36-5 in an amount of 0,675 g/900 ml test solution.

Detergent A comprises 3.5% (w/w) of the active ingredient in Bardap-26 (CAS NR 94667-33-1). Thereby test solution 4 comprises CAS 94667-33-1 in an amount of 0.21 g/900 ml test solution.

Detergent A comprises 1.25% (w/w) of the active ingredient in Akacid Forte (CAS NR 57028-96-3). Thereby test solution 4 comprises CAS 57028-96-3 in an amount of 0,075 g/900 ml test solution.

In total, test solution 4 comprises biocides in the amount of (0.21+0.075) g/900 ml=0,285 g biocides/900 ml test solution Test Solution 5

Detergent A with biocides (table 8a) was diluted with water to a concentration of 12 g/900 ml test solution:

Detergent A comprises 11.25% (w/w) of the active ingredient in Lutensol TO 89 (CAS nr. 69011-36-5). Thereby test solution 5 comprises CAS nr. 69011-36-5 in an amount of 1.35 g/900 ml test solution.

Detergent A comprises 3.5% (w/w) of the active ingredient in Bardap-26 (CAS NR 94667-33-1). Thereby test solution 4 comprises CAS 94667-33-1 in an amount of 0.42 g/900 ml test solution.

Detergent A comprises 1.25% (w/w) of the active ingredient in Akacid Forte (CAS NR 57028-96-3). Thereby test solution 4 comprises CAS 57028-96-3 in an amount of 0.15 g/900 ml test solution.

In total, test solution 5 comprises biocides in the amount of (0.42+0.15) g/900 ml=0.57 g biocides/900 ml test solution Test Solution 6

Detergent B without biocides (table 8d) was diluted with water to a concentration of 5.4 g/liter test solution:

Detergent B comprises 11.25% (w/w) of the active ingredient in Marlipal 24/939 (CAS-NR 68439-50-9). Thereby test solution 6 comprises CAS-NR 68439-50-9 in an amount of 0.61 g/liter test solution.
Test solution comprises no biocide.
Test Solution 7
Detergent B with biocides (table 8c) was diluted with water to a concentration of 6 g/900 ml test solution:
Detergent B comprises 11.25% (w/w) of the active ingredient in Marlipal 24/939 (CAS-NR 68439-50-9). Thereby test solution 7 comprises CAS-NR 68439-50-9 in an amount of 0,675 g/900 ml test solution.
Detergent B comprises 3.5% (w/w) of the active ingredient in Bardap-26 (CAS NR 94667-33-1). Thereby test solution 4 comprises CAS 94667-33-1 in an amount of 0.21 g/900 ml test solution.
Detergent B comprises 1.25% (w/w) of the active ingredient in Akacid Forte (CAS NR 57028-96-3). Thereby test solution 4 comprises CAS 57028-96-3 in an amount of 0,075 g/900 ml test solution.
In total, test solution 7 comprises biocides in the amount of (0.21+0.075) g/900 ml=0,285 g biocides/900 ml test solution
Test Solution 8
Detergent B with biocides (table 8c) was diluted with water to a concentration of 12 g/900 ml test solution:
Detergent B comprises 11.25% (w/w) of the active ingredient in Marlipal 24/939 (CAS-NR 68439-50-9). Thereby test solution 8 comprises CAS nr. CAS-NR 68439-50-9 in an amount of 1.35 g/900 ml test solution.
Detergent B comprises 3.5% (w/w) of the active ingredient in Bardap-26 (CAS NR94667-33-1). Thereby test solution 4 comprises CAS 94667-33-1 in an amount of 0.42 g/900 ml test solution.
Detergent B comprises 1.25% (w/w) of the active ingredient in Akacid Forte (CAS NR 57028-96-3). Thereby test solution 4 comprises CAS 57028-96-3 in an amount of 0.15 g/900 ml test solution.
In total, test solution 8 comprises biocides in the amount of (0.42+0.15) g/900 ml=0.57 g biocides/900 ml test solution
Experimental
9 ml of test solution 1, 2, 3, 4, 5, 6, 7 or 8 was added into a sterile test tube. 1 ml of bacterial stock culture or yeast stock culture was added immediately before exposure.
Thus, the concentration during exposure was as follows:

TABLE 10

Exposure concentrations

| Product | Concentration | Concentration (ppm) during exposure | | | | | | | |
|---|---|---|---|---|---|---|---|---|---|
| | | 1 | 2 | 3 | 4 | 5 | 6 | 7 | 8 |
| Lutensol TO 89 | CAS nr. 69011-36-5* | — | — | 610 | 675 | 1350 | — | — | — |
| Marlipal 24/939 | CAS-NR 68439-50-9** | — | — | — | — | — | 610 | 675 | 1350 |
| Bardap-26 | CAS NR 94667-33-1*** | 300 | 600 | — | 210 | 420 | — | 210 | 420 |
| Akacid Forte | CAS NR 57028-96-3**** | 300 | 600 | — | 75 | 150 | — | 75 | 150 |
| Total biocides | | 600 | 1200 | | 285 | 570 | | 285 | 570 |

Test solutions were exposed to micro organisms for 9 minutes at 30° C.
The number of surviving bacteria was determined immediately after exposure. The bacterial CFU (colony forming units) after exposure to bacteria was carried out using normal plate counts on TSA plates (Tryptic Soy Agar) at 37° C. for 24 hours. Counts of yeast CFU after exposure was carried out using normal plate counts on MEA at 37° C. for 48 hours.
All tests were performed in triplicate.
Results and Conclusion:

TABLE 11

Results from exposure

| Test solution | Candida albicans | Staph. aureus | E. coli |
|---|---|---|---|
| 1 | ~$10^6$ | ~$10^7$ | ~$10^7$ |
| 2 | >$10^6$ | ~$10^7$ | ~$10^7$ |
| 3 | <10 | None | None |
| 4 | >$10^5$ | ~$10^7$ | ~$10^7$ |
| 5 | >$10^6$ | ~$10^7$ | ~$10^7$ |
| 6 | <10 | None | None |
| 7 | >$10^5$ | ~$10^7$ | ~$10^7$ |
| 8 | >$10^6$ | ~$10^7$ | ~$10^7$ |

When incorporating detergent C comprising Plurafac LF 300 (prepared in accordance with example 7) into a test solution comprising Bardap-26 and Akacid Forte, then reductions as low as $10^2$ of yeast are obtained.
The results show that (table 11):
A reduction of $10^5$ of yeast was obtained at the lower biocide concentration present in test solutions 4 and 7.
A reduction of $10^6$ of yeast was obtained t the higher biocide concentration present in test solutions 4 and 7.
A reduction of $10^7$ of bacteria was obtained at the biocide concentration of test solutions 5 and 8
The same reduction was obtained for all test solutions when exposed to *Staph. Aureus* and *E. coli.*
The same results were obtained for Lutensol TO 89 and Marlipal 24/939
There is no difference in the reduction of bacteria obtained for test solutions 1 and 2 as compared to test solutions 4, 5, 6 and 7
There is no difference in the reduction of yeast obtained for test solutions 1 and 2 as compared to test solutions 5 and 8

The addition of Lutensol TO 89 and Marlipal 24/939 did not have any significant impact on the biocide effect of the biocides No reduction of the tested organisms was seen when exposed to test solutions 3 and 6.

Addition of Plurafac LF300 comprised in detergent C leads to a reduction of yeast as low as a factor 100.

A reduction as high as $10^5$ of yeast was obtained after exposure to the biocidal detergent compositions wherein the biocide concentration was as low as 285 ppm. Accordingly, in a non-limiting example, exposure under the same conditions to biocidal compositions wherein the biocide concentration was as high as 600 or 1200 ppm without detergent only increased the reduction of yeast with a factor 10 to a reduction of yeast of $10^6$.

In one embodiment, the same reduction of yeast was obtained when exposing to a biocidal composition without detergent and when exposing to a biocidal detergent composition. Accordingly, in a non-limiting example, the same reduction of $10^6$ of yeast was obtained after exposure to biocidal detergent compositions comprising 570 ppm biocide and 600 or 1200 ppm biocide composition without detergent.

In one embodiment, at least the same antibacterial effect was obtained when exposing to a biocidal composition without detergent and when exposing to a biocidal detergent composition. Accordingly, in a non-limiting example, the same reduction of $10^7$ of bacteria was obtained after exposure to biocidal detergent compositions comprising 285 or 570 ppm biocide and 600 or 1200 ppm biocide composition without detergent.

The same reduction was obtained independently of the bacteria tested.

Conclusion

Based on the above results, it is concluded that addition of Lutensol TO 89 and Marlipal 24/939 does not significantly have an impact on the biocide effect of Marlipal 24/939 and Bardap-26.

Example 9

Test Solutions

Detergent A with biocides and detergent B with biocides obtained from Example 7 tables 8a+c were tested.

Furthermore a solution comprising

| | |
|---|---|
| Water | 75% (w/w); and |
| Akacid Forte was tested | 25% (w/w) |

Experimental

The critical micelle concentration is measured using Sudan Black B dissolved in the test solutions at different concentrations. Sudan Black B is dissolvable in micelles, only. A difference in the absorbance measured is thus a valid measure of the critical micelle concentration in the test solutions.

Sudan black is of the below structure:

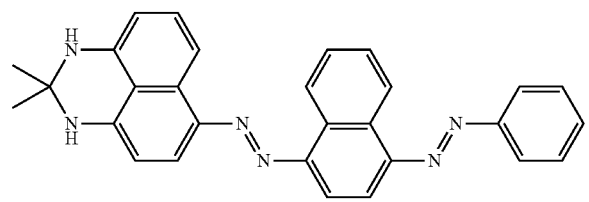 [SMILES: CC1(C)Nc2cccc3c(/N=N/c4ccc(/N=N/c5ccccc5)c5ccccc45)ccc(c23)N1]

Absorbance was measured using a Shimadzu UV-1800 spectrofotometer and the absorbance is measured at 600 nm.

Dilutions were made in water and Sudan Black B by adding first water, then Sudan Black B and at last the test solutions to 4 ml cuvettes. The dilutions were then stirred and left for at least 6 hours at room temperature. Then the absorbance was measured.

Results

CMC for Detergent A (Table 8a)
  CMC for diluted Detergent A (table 8a) was measured to 0,097 g/l (FIGS. 1 and 2)
  Detergent A (table 8a) comprises 11.25% (w/w) of the active ingredient in Lutensol TO 89 (CAS nr. 69011-36-5). Thereby, diluted detergent A comprises CAS nr. 69011-36-5 in an amount of 10.9 mg/l solution.

CMC for Detergent B (Table 8c)
  CMC for diluted Detergent B (table 8c) was measured to 0.03 g/l (FIGS. 3 and 4)
  Detergent B (table 8a) comprises 11.25% (w/w) of the active ingredient in Marlipal 24/939 (CAS-NR 68439-50-9). Thereby diluted detergent B comprises CAS-NR 68439-50-9 in an amount of 3.38 mg/l solution.

CMC for Akacid Forte
  CMC for diluted Akacid Forte was measured to 15 g/l (FIGS. 5 and 6)
  This 15 g/l dilution is diluted from a 25% (w/w) solution of Akacid Forte and thus comprises 3.75 g/l. Akacid Forte comprises the active ingredient CAS 57028-96-3 in an amount of 25% (w/w). Thereby the 15 g/l dilution comprises CAS 57028-96-3 in an amount of 0,938 g/l CMC for Bardap-26 is about 0.7-1.0 mmol/l (data not shown)

The invention claimed is:

1. A composition comprising a mixture of the biocides Poly-(hexamethylene-guanidium chloride) and N,N-didecyl-N-methyl-poly(oxyethyl) ammonium propionate, said biocides having synergistic effect in regard to the total biocidal activity, wherein said composition does not comprise a surfactant.

2. A detergent composition comprising a mixture of the biocides Poly-(hexamethylene-guanidium chloride) and N,N-didecyl-N-methyl-poly(oxyethyl)ammonium propionate, said biocides having synergistic effect in regard to the total biocidal activity and one or more surfactants selected from the group consisting of non-ionic surfactants and monovalent cationic surfactants, wherein said one or more surfactants are of the general formula (I):

R(OCH$_2$CH$_2$)xOH wherein
  i) R is $C_{7-20}$-alkyl whereby the alkyl is of 7-20 carbon atoms; wherein R is optionally substituted with:
    a) one or more substituents selected from the group consisting of alkyl, $C_{3-8}$-cycloalkyl, $C_{3-8}$-cycloalkyl-$C_{1-6}$-alkyl, $C_{1-6}$-alkyl-$C_{3-8}$-cycloalkyl, aryl-$C_{1-6}$-alkyl, $C_{1-6}$-alkyl-aryl, $C_{1-6}$-alkyl-oxy, $C_{3-8}$-cycloalkyl-oxy, $C_{3-8}$-cycloalkyl-$C_{1-6}$-alkyl-oxy, $C_{3-8}$-cycloalkyl-oxy-$C_{1-6}$-alkyl, $C_{1-6}$-alkyl-oxy-$C_{3-8}$-cycloalkyl, $C_{1-6}$-alkyl-$C_{3-8}$-cycloalkyl-oxy, aryl-$C_{1-6}$-alkyl-oxy, and aryl; or
    b) one or two groups selected from the group consisting of —$C_{7-20}$-alkyl(OCH$_2$CH$_2$)$_y$OH and —$C_{7-20}$-alkyl(OCH$_2$CH$_2$)$_z$OH;
      wherein each of y and z is an integer selected from 2-12;
      whereby the polyethyleneglycol comprises 2-12 repetitions of OCH$_2$CH$_2$; and ii) x is an integer selected from 2-12, whereby the polyethyleneglycol comprises 2-12 repetitions of $OCH_2CH_2$; and iii) with the proviso that when R is $C_{18}$-alkyl then
   y is not greater than x; and
   z is not greater than x; and
   the surfactant may not comprise an alkoxylated moiety that comprises higher alkoxides than the ethylene oxides.

3. The composition according to claim 2, which further comprises
   i) one or more liquid carriers; and
   ii) one or more chelating agents.

4. The composition according to claim 2, wherein x is 4-8.

5. The composition according to claim 2, wherein R is $C_{12-14}$-alkyl.

6. The composition according to claim 2, wherein at least 80% by weight of R is $C_{12}$-alkyl, $C_{13}$-alkyl or $C_{14}$-alkyl or mixtures thereof.

7. The composition according to claim 2, said composition comprising a surfactant of formula (I) wherein R is substituted with one or more substituents selected from the group consisting of
$C_{1-6}$-alkenyl, $C_{1-6}$-alkynyl, $C_{3-8}$-cycloalkenyl, $C_{3-8}$-cycloalkenyl-$C_{1-6}$-alkenyl, $C_{3-8}$-scycloalkenyl-$C_{1-6}$-alkynyl, $C_{1-6}$-alkenyl-$C_{3-8}$-cycloalkenyl, $C_{1-6}$-alkynyl-$C_{3-8}$-cycloalkenyl, aryl-$C_{1-6}$-alkenyl, aryl-$C_{1-6}$-alkynyl, $C_{1-6}$-alk enyl-aryl, $C_{1-6}$-alkynyl-aryl, $C_{1-6}$-alkenyl-oxy, $C_{1-6}$-alkynyl-oxy, $C_{3-8}$-cycloalkenyl-oxy, $C_{3-8}$-cycloalkenyl-$C_{1-6}$-alkenyl-oxy, $C_{3-8}$-scycloalkenyl-$C_{1-6}$-alkynyl-oxy, C3-s-cycloalkenyl-oxy-$C_{1-6}$-alkenyl, $C_{3-8}$-cycloalkenyloxy-$C_{1-6}$-alkynyl, $C_{1-6}$-alkenyl-oxy-$C_{3-8}$-cycloalkenyl, $C_{1-6}$-alkynyl-oxy-$C_{3-8}$-cycloalkenyl, $C_{1-6}$-alkenyl-$C_{3-8}$-cycloalkenyl-oxy, $C_{1-6}$-alkynyl-$C_{3-8}$-cycloalkenyl-oxy, aryl-$C_{1-6}$-alkenyloxy, aryl-$C_{1-6}$-alkenyl-oxy, aryl-oxy-$C_{1-6}$-alkenyl, aryl-oxy-$C_{1-6}$-alkynyl and aryl.

8. The composition according to claim 2, said composition comprising a surfactant of formula (I) wherein R is substituted with one or two groups selected from —$C_{7-20}$-alkyl-$(OCH_2CH_2)_y$OH and —$C_{7-20}$-alkyl-$(OCH_2CH_2)_z$OH.

9. The composition according to claim 2, said composition comprising a surfactant of formula (I) wherein R is not substituted.

10. The composition according claim 2, wherein the one or more surfactants are selected from the group consisting of nonionic surfactants.

11. The composition according to claim 2, wherein the one or more surfactants are selected from the group consisting of a $C_{12-14}$ alcohol polyethylene glycol ether mixture.

12. The composition according to claim 2, said composition comprising only one surfactant which is selected from the group consisting of a $C_{12-14}$ alcohol polyethylene glycol ether mixture.

13. The composition according to claim 2, said composition comprising only one surfactant which is selected from the group consisting of iso-$C_{12-14}$ alcohol ethoxylates and combinations thereof.

14. The composition according to claim 2, which is characterized in that CMC(biocid)>MIC(biocid).

15. The composition according to claim 2, which is characterized in that CMC(detergent)>MIC(biocid).

16. The composition according to claim 1, said composition comprising one or more liquid carriers selected from the group consisting of water, ethanol, glycerol, propylene glycol, glycerin, and combinations thereof.

17. The composition according to claim 1, said composition comprising one or more liquid carriers selected from propylene glycol and water and mixtures thereof.

18. The composition according to claim 1, said composition comprising one or more chelating agents selected from the group consisting of amino-tri(methylene) phophonic acid sodium salt (ATMP), methylglycinediacetic acid, potassium tripolyphosphate, and combinations thereof.

19. The composition according to claim 2, wherein the composition is suitable for washing at low temperatures in a range of 5° C. to 40° C.

20. The composition according claim 2, wherein the composition is a delicate laundry detergent composition.

21. The composition according to claim 2, wherein the composition is for washing of clothing or textiles considered to be a source of infection.

22. The composition according to claim 2, wherein the composition does not comprise enzymes.

23. The composition according to claim 2, which is a liquid laundry detergent.

24. The composition according to claim 1, for use as:
   a) disinfectants and general biocidal products;
   b) preservatives;
   c) pest control;
   d) preservatives for food or feedstocks;
   e) antifouling products;
   f) embalming and taxidermist fluids; and control of other vertebrates
   g) vermin control on domestic animals, livestock or pets
   h) alga control; or
   i) products for use in spas or swimming pools.

25. The composition according to claim 2, said composition comprising only one surfactant which is selected from the group consisting of a mixture of fatty alcohols with 9 mol ethylene oxide and fatty alcohols with 3 mol ethylene oxide.

26. The composition according claim 10, wherein the one or more surfactants are alkoxylated nonionic surfactants.

27. The composition according to claim 11, wherein the one or more surfactants are selected from the group consisting of a mixture of fatty alcohols with 9 mol ethylene oxide, fatty alcohols with 3 mol ethylene oxide, and iso-C13 alcohol ethoxylate, and combinations thereof.

28. The composition according to claim 12, wherein the mixture is a mixture of fatty alcohols with 9 mol ethylene oxide and fatty alcohols with 3 mol ethylene oxide.

29. The composition according to claim 13, said composition comprising the surfactant is iso-C13 alcohol ethoxylate.

30. A composition comprising a mixture of the biocides Poly-(hexamethylene-guanidium chloride) and N, N-didecyl-N-methyl-poly(oxyethyl) ammonium propionate, said biocides having synergistic effect in regard to the total biocidal activity.

31. The composition according to claim 30, said composition comprising one or more liquid carriers selected from the group consisting of water, ethanol, glycerol, propylene glycol, glycerin, and combinations thereof.

32. The composition according to claim 30, said composition comprising one or more liquid carriers selected from propylene glycol and water and mixtures thereof.

33. The composition according to claim 30, said composition comprising one or more chelating agents selected from the group consisting of amino-tri(methylene) phophonic acid sodium salt (ATM)), methylglycinediacetic acid, potassium tripolyphosphate, and combinations thereof.

34. The composition according to claim 30, for use as:
a) disinfectants and general biocidal products;
b) preservatives;
c) pest control;
d) preservatives for food or feedstocks;
e) antifouling products;
f) embalming and taxidermist fluids; and control of other vertebrates
g) vermin control on domestic animals, livestock or pets
h) alga control; or
i) products for use in spas or swimming pools.

* * * * *

UNITED STATES PATENT AND TRADEMARK OFFICE
CERTIFICATE OF CORRECTION

| | |
|---|---|
| PATENT NO. | : 9,719,057 B2 |
| APPLICATION NO. | : 14/870316 |
| DATED | : August 1, 2017 |
| INVENTOR(S) | : Nielsen et al. |

It is certified that error appears in the above-identified patent and that said Letters Patent is hereby corrected as shown below:

In the Claims

In Column 44, Line 65 replace "phonic acid sodium salt (ATM))," with "phonic acid sodium salt (ATMP),"

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*